US00RE37303E

(19) United States

(12) Reissued Patent

Schwartz et al.

(10) Patent Number: US RE37,303 E

(45) Date of Reissued Patent: Jul. 31, 2001

(54) IMIDAZOLE COMPOUNDS AND THEIR THERAPEUTIC APPLICATIONS

(75) Inventors: Jean-Charles Schwartz, Paris; Jean-Michel Arrang, Gif sur Yvette; Monique Garbarg; Jeanne-Marie Lecomte, both of Paris, all of (FR); Charon R. Ganellin, Welwyn (GB); Abdellatif Fkyerat, La Bassee (FR); Wasyl Tertiuk, Welwyn Garden City (GB); Walter Schunack, Berlin (DE); Ralph Lipp, Berlin (DE); Holger Stark, Berlin (DE); Katja Purand, Berlin (DE)

(73) Assignees: Institut National del la Sante et de la Recherche Medicale; Societe Civile Bioprojet, both of (FR)

(21) Appl. No.: 09/544,755

(22) PCT Filed: Jan. 8, 1993

(86) PCT No.: PCT/FR93/00015

§ 371 Date: Jan. 28, 1994

§ 102(e) Date: Jan. 28, 1994

(87) PCT Pub. No.: WO93/14070

PCT Pub. Date: Jul. 22, 1993

Related U.S. Patent Documents

Reissue of:

(64) Patent No.: 5,559,113
Issued: Sep. 24, 1996
Appl. No.: 08/117,161
Filed: Jan. 8, 1993

(30) Foreign Application Priority Data

Jan. 10, 1992 (FR) ..... 92 00189

(51) Int. Cl.[7] ..... A61K 31/4178; C07D 233/64; C07D 233/84; C07D 401/12; C07D 403/12; C07D 417/12

(52) U.S. Cl. ..... 514/252; 514/255; 514/272; 514/341; 514/365; 514/397; 514/398; 514/399; 514/400; 544/324; 544/370; 546/272.7; 546/275.1; 546/270.4; 546/274.1; 548/311.1; 548/312.4; 548/314.4; 548/315.1; 548/315.4; 548/326.1; 548/335.5; 548/339.1; 548/171

(58) Field of Search ..... 514/252, 255, 514/272, 341, 365, 397, 398, 399, 400; 544/324, 370; 546/272.7, 275.1, 274.1, 270.4; 548/311.1, 312.4, 314.4, 315.1, 315.4, 326.1, 335.5, 339.1, 171

(56) References Cited

U.S. PATENT DOCUMENTS

| | | | | |
|---|---|---|---|---|
| 2,252,721 | * | 8/1941 | Miescher et al. | 548/311.1 X |
| 2,301,532 | * | 11/1942 | Fell, I | 548/336.1 X |
| 2,376,424 | * | 5/1945 | Fell, II | 548/336.1 X |
| 3,950,333 | * | 4/1976 | Durant, I et al. | 548/336.1 X |
| 4,083,988 | * | 4/1978 | Durant, II et al. | 424/273 R |
| 4,154,834 | * | 5/1979 | Brown, I et al. | 424/251 |
| 4,304,780 | * | 12/1981 | Martin-Smith et al. | 424/263 |
| 4,489,089 | * | 12/1984 | Wright et al. | 424/273 R |
| 4,540,699 | * | 9/1985 | Brown, II et al. | 514/272 |
| 4,996,221 | * | 2/1991 | Melmon et al. | 514/399 |

FOREIGN PATENT DOCUMENTS

| | | | | |
|---|---|---|---|---|
| 0514574 | * | 10/1978 | (AU) | 548/336.1 |
| 0276541 | * | 7/1914 | (DE) | 548/336.1 |
| 0332955 | * | 2/1951 | (DE) | 548/336.1 |
| 0522291 | * | of 0000 | (EP) | 514/396 |
| 0468702 | * | 1/1919 | (EP) | 514/396 |
| 0041359 | * | 12/1981 | (EP) | 548/336.1 |
| 0054865 | * | 6/1982 | (EP) | 548/336.1 |
| 0081324 | * | 6/1983 | (EP) | 548/336.1 |
| 0199845 | * | 11/1986 | (EP) | 548/336.1 |
| 0262448 | * | 4/1988 | (EP) | 548/336.1 |
| 0291172 | * | 11/1988 | (EP) | 548/336.1 |
| 0302164 | * | 2/1989 | (EP) | 548/336.1 |
| 0302692 | * | 2/1989 | (EP) | 514/396 |
| 0315316 | * | 5/1989 | (EP) | 548/336.1 |
| 0338939 | * | 10/1989 | (EP) | 548/336.1 |
| 1220002 | * | 1/1960 | (FR) | 548/336.1 |
| 2100822 | * | 3/1972 | (FR) | 548/336.1 |
| 1305548 | * | 2/1973 | (GB) | 548/336.1 |
| 1305549 | * | 2/1973 | (GB) | 548/336.1 |
| 1305647 | * | 2/1973 | (GB) | 548/336.1 |
| 1341375 | * | 12/1973 | (GB) | 548/336.1 |
| 1531221 | * | 11/1978 | (GB) | 548/336.1 |
| 2110663 | * | 6/1983 | (GB) | 548/336.1 |
| 87-07891 | * | 12/1987 | (WO) | 548/336.1 |
| 89-10360 | * | 11/1989 | (WO) | 548/336.1 |

OTHER PUBLICATIONS

European Search Report No.—9212285.*

* cited by examiner

*Primary Examiner*—Floyd D. Higel

(74) *Attorney, Agent, or Firm*—Bierman, Muserlian and Lucas

(57) ABSTRACT

A compound selected from the group consisting of a compound of the formula

IA and

IB wherein the substituents are defined as in the specification having antagonist properties to histamine $H_3$-receptors.

13 Claims, No Drawings

IMIDAZOLE COMPOUNDS AND THEIR THERAPEUTIC APPLICATIONS

Matter enclosed in heavy brackets [ ] appears in the original patent but forms no part of this reissue specification; matter printed in italics indicates the additions made by reissue.

The present invention relates to novel imidazole derivatives, to their preparation and to their therapeutic applications.

The imidazole derivatives in accordance with the invention show useful antagonist properties for histamine $H_3$ receptors which control the release and synthesis of histamine. Their antagonist activity on the $H_3$ receptors makes them useful in therapeutics, in particular as a medicament possessing sedative, sleep regulating, anticonvulsant, psychostimulating, cerebral circulation modulating and anti-ulcer effects.

The derivatives in accordance with the invention correspond to the general formula IA or IB

IA

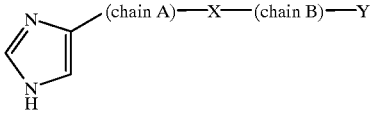

IB

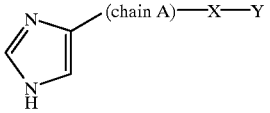

in which the chain A represents a saturated or unsaturated, straight or branched hydrocarbon chain containing 1 to 6 carbon atoms, it being possible for the saturated hydrocarbon chain to be interrupted by a hetero atom such as a sulphur atom, X represents an oxygen or sulphur atom, —NH—, —NHCO—, —N(alkyl)CO—, —NHCONH—, —NH—CS—NH—, —NHCS—, —O—CO—, —CO—O—, —OCONH—, —OCON(alkyl)—, —OCONH—CO—, —CONH—, —CON(alkyl)—, —SO—, —CO—, —CHOH— or —NR—C(=NR")—NR'—, R and R' denoting a hydrogen atom or a lower alkyl radical and R" a hydrogen atom or another powerful electronegative group, such as a cyano or $COY_1$ group, $Y_1$ denoting an alkoxy group, the chain B represents a straight alkylene chain $—(CH_2)_n—$, n being an integer which can vary between 0 and 5 or a branched alkylene chain containing from 2 to 8 carbon atoms, it being possible for the alkylene chain to be interrupted by one or a number of oxygen or sulphur atoms, or a group $—(CH_2)_n—O—$ or $—(CH_2)_n—S—$ where n is an integer equal to 1 or 2, Y represents a straight or branched alkyl group containing 1 to 8 carbon atoms, a cycloalkyl containing 3 to 6 carbon atoms, a bicycloalkyl group, a cycloalkenyl group, an aryl group such as an optionally substituted phenyl group, a 5- or 6-membered heterocyclic radical containing one or two heteroatoms chosen from nitrogen and sulphur atoms, the said heterocyclic radical optionally being substituted, or also a bicyclic radical resulting from the fusion of a benzene ring to a heterocycle as defined above.

The chain A can be a straight alkylene chain $—(CH_2)_n—$, n representing an integer between 0 and 6 carbon atoms, preferably between 1 and 4 carbon atoms, or a branched alkylene chain, preferably a chain substituted by one or a number of methyl or ethyl radicals.

The chain A can also be a straight or branched alkylene chain, and can be, for example, the allyl group.

When Y represents a cycloalkyl group, the latter can be, for example, cyclopentyl, cyclohexyl or a bicycloalkyl group.

When Y represents a substituted phenyl group, the phenyl group can be mono- or polysubstituted, for example, by a halogen, by a lower alkyl, for example $CH_3$, by $CF_3$, CN, $COCH_3$, $COOR_1$ or $OR_1$, $R_1$ representing a lower alkyl, for example $COOCH_3$, the $NO_2$ group or the group $NR_2R_3$, $R_2$ and $R_3$ representing a hydrogen atom and/or a lower alkyl radical ("lower alkyl" means an alkyl radical containing at most 6 carbon atoms).

When Y represents a heterocyclic radical, the latter can be, for example, the pyridyl radical, the pyridyl N-oxide radical or the pyrazinyl radical, optionally mono- or polysubstituted by $NO_2$, $CF_3$, $CH_3$, $NH_2$, a halogen such as Cl, the $COOCH_3$ group or also the imidazolyl or thiazolyl radical.

When Y represents a bicyclic radical resulting from the fusion of a benzene ring to a heterocycle, the radical can be, for example, the benzothiazyle radical.

The compounds which correspond to the formula IA or IB are novel compounds, with the exception, however:

a) of the compounds in which X represents —NH—, the chain A the $—(CH_2)_2—$ group, the chain B the $—(CH_2)_2—O—$ group or the group $—(CH_2)_n—S—$ and Y the phenyl or p-chloro phenyl group, b) of the compounds in which X represents the —NHCO— group, the chain A the $—(CH_2)_2—$ group and Y the methyl group (formula IB) or the chain B and Y (formula IA) represent a straight alkylene chain $—(CH_2)_n—$, n being between 1 and 4, the $—CH_2—O—$ or $—CH_2—S—CH_2—$ groups and a phenyl group, or also the $—CH_2—CH_2—$ or $—CH_2—S—CH_2—$ groups and the diphenyl group, or also the $—(CH_2)_3—$ or $—CH_2—S—CH_2—$ groups and the pyridyl group, or also the $—CH_2—CH_2—$ or $—CH_2—S—$ groups and the diphenyl group, or else the $—(CH_2)_3—$ group and the imidazolyl or cyclohexyl group, c) of the compounds in which X represents —NHCO—, the chain A the $—CH_2—CH(CH_3)—$ group, the chain B the $—(CH_2)_3—$ group and Y the phenyl group, d) of the compounds in which X represents —NHCSNH— or —NHCONH—, the chain A the $—(CH_2)_2—$ group, the chain B the $—(CH_2)_2—$ group and Y the phenyl group, e) of the compounds in which the chain A represents a straight saturated hydrocarbon chain containing 1 to 6 carbon atoms, X represents —NH—, the chain B represents an alkylene chain as defined above and Y represents a phenyl group or an imidazolyl radical, as well as those in which A represents a straight saturated hydrocarbon chain containing 1 to 6 carbon atoms, X represents the —NHCONH— group, the chain B and/or Y represent an alkyl and Y represents an aryl radical;

f) of the compounds in which X represents an oxygen atom, the chain A a $—CH_2—$ group and Y a substituted phenyl group (formula IB);

g) of the compounds in which X represents the —NHCO— group, the chain A the $—(CH_2)_2—$ group and Y a substituted cyclohexyl group (formula IB);

h) of the compounds in which X represents the —NH—CS—NH— group, the chain A the group $—(CH_2)_n—$ (n=3 to 6) and Y an alkyl, aryl and aralkyl group (formula IB);

i) of the compounds in which X represents the —CO— group, the chain A the —$(CH_2)_2$— group and Y an optionally substituted aryl radical, a 5-membered heterocyclic radical containing sulphur as heteroatom and optionally substituted, or a bicyclic radical resulting from the fusion of a benzene ring to a 5- or 6-membered heterocycle containing nitrogen and/or sulphur atoms as hetero atoms (formula IB);

j) of the compounds in which X represents the —CONH— group, the chain A the —$(CH_2)_2$— group and Y the optionally substituted phenyl group (formula IB);

k) of the compounds in which X represents the —NH—C(═NCN)—NH— group, the chain A a hydrocarbon chain containing 2 to 4 C atoms interrupted by an S atom and Y a 5- or 6-membered heterocycle containing one or two nitrogen and sulphur atoms (formula IB);

l) of the compounds in which X represents the —NH—C(═NCN)—NH— group, the chain A a —$CH_2$—S—$(CH_2)_2$— group and Y a methyl radical (formula IB);

m) of the compounds in which X represents the —NH—C(═NH)—NH— group, the chain A and chain B have the abovementioned meaning and Y represents an alkyl group, an aryl group, or a 5- or 6-membered heterocyclic radical containing one or two heteroatoms which can be nitrogen and/or sulphur.

The compounds set out under a) to d) were disclosed during a symposium which was held at Budapest in August 1988 ("10th International Symposium on Medicinal Chemistry") and more recently at Noordwijkerhout (July 1990).

The compounds set out under e) have been described in Patent GB 1,341,375; the compounds set out under f) in French patent No. 1,220,002; the compounds set out under g) in U.S. Pat. Nos. 2,301,532 and 2,376,424; the compounds set out under h) in Patent GB 1,305,547; the compounds set out under i) in European Patent Application EP-A-0,291,172; the compounds set out under j) in European Patent Application EP-A-315,316; the compounds set out under k) in Patent GB 1,531,221 and the compounds set out under l) in Australian Patent AU-A-514,574; the compounds set out under m) in European Patent Applications EP-A-0,199,845 and EP-A-0,262,448.

The present invention also relates to the addition salts which the compounds of formula IA or IB form with pharmaceutically acceptable acids. The pharmaceutically acceptable salts comprise the nontoxic salts of inorganic or organic acids such as the hydrochloride, the hydrobromide or the maleate.

The present invention also encompasses the hydrates of the compounds of formula IA or IB, the hydrated salts of these compounds and the polymorphic crystalline structures. It is necessary, moreover, to note that the structure of the compounds in accordance with the invention, as it is illustrated by the formulae IA and IB, only represents one of the possible tautomeric forms of these compounds and that the latter can exist under other tautomeric forms. The present invention thus also encompasses all the possible tautomeric forms of the compounds in question, whether these tautomers exist in the isolated form or in the form of mixtures.

The compounds of formula IA or IB can exist in one or a number of isomeric forms according to the number of asymmetric centres in the molecule. The invention thus relates both to all the optical isomers and to their racemic modifications and the corresponding diastereoisomers. The separation of the diastereoisomers and/or of the optical isomers can be carried out according to methods known per se.

The compounds of formula IA or IB in which X represents —NH—, the chain A, the chain B and Y having the abovementioned meanings, are obtained, for example, by reacting an amine of formula

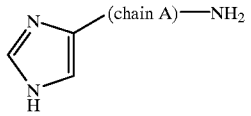

with a halogenated compound of formula

Hal-(chain B)-Y or

Hal-Y

Hal denoting a halogen such as chlorine or bromine, in the presence of a solvent.

The compounds of formula IA or IB in which X represents —NHCO—, the chain A, the chain B and Y having the abovementioned meanings, are obtained, for example, by reacting an amine of formula

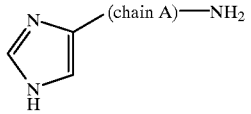

with an acid of formula

HOOC-(chain B)-Y or

HOOC-Y after optional activation of the hydroxyl functional group of this acid.

The compounds of formula IA in which X represents —NH— and corresponding to the general formula

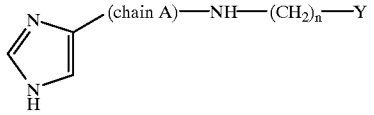

the chain A, Y and n having the abovementioned meanings, can also be obtained by reducing the carbonyl group in the compound of formula

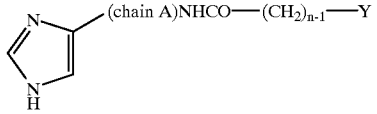

for example using a hydride such as sodium borohydride.

The compounds of formula IA in which X represents —NH—, the chain B represents —$(CH_2)_n$—S—, n being between 1 and 4, the chain A and Y having the abovementioned meanings, are obtained by treating a compound of formula

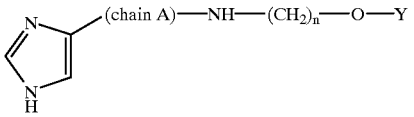

with a halogenated hydracid, such as hydrobromic acid, to form the halogenated compound

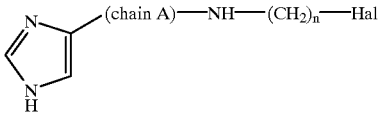

Hal denoting a halogen,
and by reacting a compound of formula

HS-Y with this halogenated compound.

The compounds of formula IA or IB in which X represents —NHCS—, the chain A, the chain B and Y having the abovementioned meanings, can be obtained by treating a compound of formula

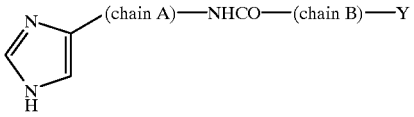

or

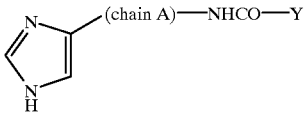

with a sulphurization agent in the presence of a solvent such as pyridine.

The compounds of formula IA or IB in which X represents —NHCONH— or —NHCSNH—, the chain A, the chain B and Y having the abovementioned meanings, can be obtained by reacting an amine, provided, for example, in the dihydrochloride form of formula

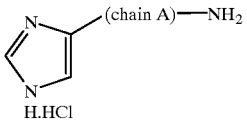

with an isocyanate of formula

OCN-(chain B)-Y or

OCN-Y or an isothiocyanate of formula

SCN-(chain B)-Y or

SCN-Y in the presence of a nonpolar solvent.

The compounds of formula IA or IB in which X represents —OCO—, the chain A, the chain B and Y having the abovementioned meanings, can be obtained by reacting an acid chloride of formula ClCO-(chain B)-Y or ClCO-Y on an alcohol, provided, for example, in the hydrochloride form, of formula

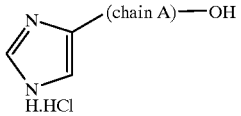

in the presence of a solvent such as pyridine.

The compounds of formula IA or IB in which X represents —CO—O—, the chain A, the chain B and Y having the abovementioned meanings, can be obtained by reacting an acid of formula

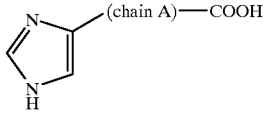

with an alcohol of formula

HO-(chain B)-Y or

HO-Y in the presence of thionyl chloride.

The compounds of formula IA or IB in which X represents —OCONH—, the chain A, the chain B and Y having the abovementioned meanings, can be obtained by reacting an alcohols, provided, for example, in the hydrochloride form, of formula

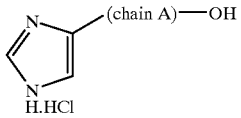

with an isocyanate of formula

OCN-(chain B)-Y or

OCN-Y in the presence of a nonpolar solvent.

The compounds of formula IA or IB in which X represents —O—, the chain A, the chain B and Y having the abovementioned meanings, can be obtained by reacting an alkoxide of formula

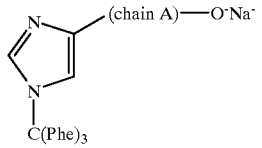

Phe denoting the phenyl radical, with a halogenated compound of formula

Hal-(chain B)-Y or

Hal-Y

Hal denoting a halogen, in the presence of a neutral solvent such as toluene, and then cleaving the —C(Phe)$_3$ group with an acid solution.

The compounds of formula IA or IB in which X represents —O—, the chain A, the chain B and Y having the abovementioned meanings, can also be obtained by reacting a halogenated compound, provided, for example, in the hydrochloride form, of formula

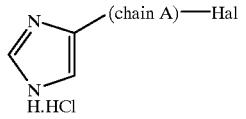

Hal denoting a halogen such as chlorine, with an alcohol of formula

HO-(chain B)-Y or

HO-Y.

The compounds of formula IB in which X represents —O—, the chain A has the abovementioned meaning and Y represents an optionally substituted phenyl group can also be obtained by reacting an alcohol of formula

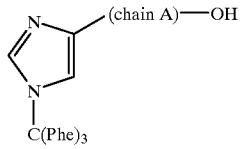

with a phenolic compound of formula

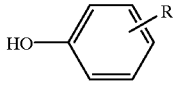

in which R represents a substituent such as a halogen, a lower alkyl, $CF_3$, CN or $COCH_3$, in the presence of triphenylphosphine and of diethyl azodicarboxylate in a solvent and by cleaving the —C(Phe)$_3$ group by treatment with an acid solution.

The compounds of formula IA or IB in which X represents —S—, the chain A, the chain B and Y having the abovementioned meanings, can be obtained by reacting an isothiourea of formula

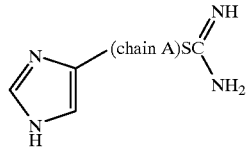

with a halogenated compound of formula

Hal-(chain B)-Y or

Hal-Y

Hal denoting a halogen such as chlorine, in the presence of a solvent such as ethanol.

The compounds of formula IA or IB in which X represents —S—, the chain A, the chain B and Y having the abovementioned meanings, can also be obtained by reacting an alcohol of formula

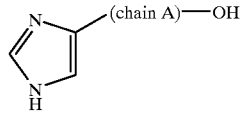

with a compound of formula

HS-(chain B)-Y or

HS-Y in the presence of a halogenated hydracid such as hydrobromic acid or by reacting a halogenated compound of formula

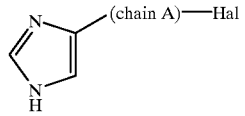

Hal denoting a halogen, with a compound of formula

HS-(chain B)-Y or

HS -Y in the presence of a base such as an alkaline hydroxide.

The compounds of formula IA or IB in which X represents —SO—, the chain A, the chain B and Y having the abovementioned meanings, can be obtained by treating a compound of formula

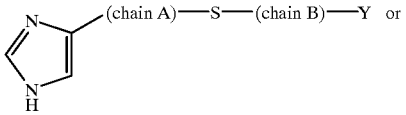

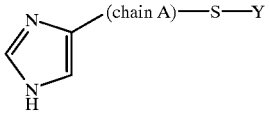

with a base such as an alkali metal or alkaline-earth metal hydroxide or carbonate in the presence of a solvent and then with an oxidizing agent.

The compounds of formula IA or IB in which X represents —CO—, the chain A, the chain B and Y having the abovementioned meanings, can be obtained by reacting a compound of formula

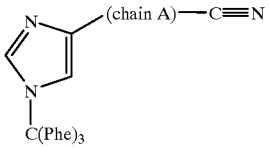

Phe denoting the phenyl radical, with

Hal-Mg-(chain B)-Y or

Hal-Mg-Y

Hal denoting a halogen, in the presence of a solvent, and then by hydrolysis of the product obtained.

The compounds of formula IA or IB in which X represents —CHOH—, the chain A, the chain B and Y having the abovementioned meanings, can be obtained by reducing the compound of formula

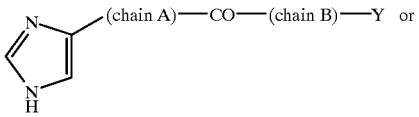

-continued

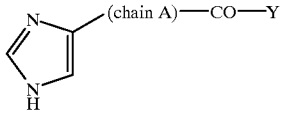

for example with a hydride, in the presence of a solvent, and then by hydrolysis with a basic solution.

The compounds of formula IA or IB in which X represents —NR—C(=NR")—NR'—, R, R', R", the chain A, the chain B and Y having the abovementioned meanings, can be obtained by reacting a compound of formula

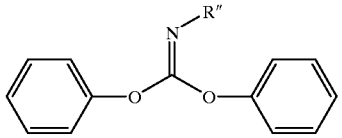

with an amine of formula $H_2N$—R'-(chain B)-Y or $H_2N$—R'—Y to form a compound of formula

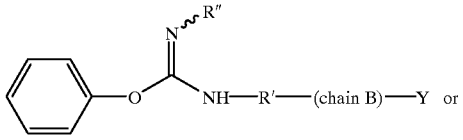

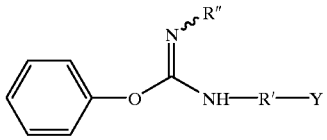

and by reacting the latter compound with an amine of formula

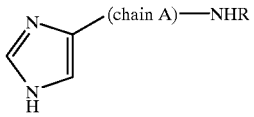

to form the compound of formula

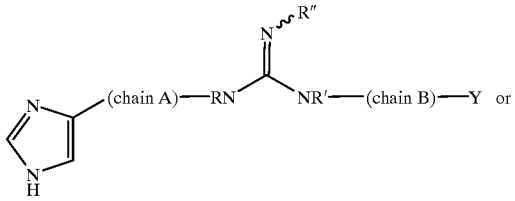

-continued

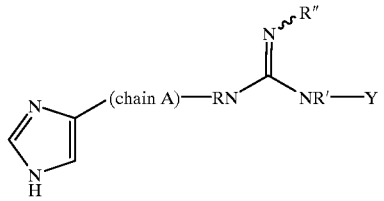

and, when R" represents hydrogen, by treating the latter compound with an acid solution to form the compound of formula

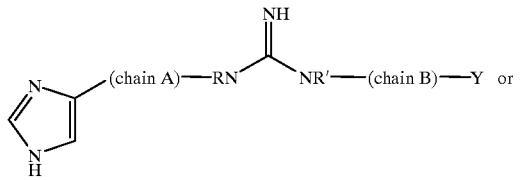

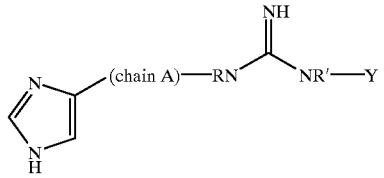

The examples which are given below, as non-limiting, illustrate the present invention.

EXAMPLE 1

N-((1H-Imidazol-4-yl)methyl)-5-phenylpentanamide 8 mmol of N,N'-carbonyldiimidazole and 8 mmol of 5-phenylpentanoic acid are introduced successively into 10 ml of absolute THF and, after having stirred for 30 min, 8 mmol of (1H-imidazol-4-yl)methanamine are added to the mixture, moisture being excluded using $CaCl_2$. At the end of 14 h, the solvent is removed by distilling under vacuum. The remaining oil is mixed with a small amount of water. The title compound is filtered under vacuum, dried and crystallized from ethanol/diethyl ether.

$C_{15}H_{19}N_3O$ (257.4) M.p.: 125°–137° C. Yield: 35%

Elemental analysis: calculated: C 70.0 H 7.44 N 16.3 found: C 70.0 H 7.52 N 16.3

EXAMPLE 2

N-(3-(1H-Imidazol-4-yl)propyl)-3-phenylpropanamide

The preparation is carried out as in Example 1 with 10 mmol of 3-phenylpropanoic acid and 3-(1H-imidazol-4-yl) propanamine as the amine component. The title compound is purified by chromatography and recrystallized in the hydrogenmaleate form from ethyl acetate/acetonitrile.

$C_{15}H_{19}N_3O.C_4H_4O_4$ (375.4) M.p.: 126°–127° C. Yield: 70%

Elemental analysis: calculated: C 60.8 H 6.71 N 11.2 found: C 61.0 H 6.30 N 11.1

EXAMPLE 3

N-(3-(1H-Imidazol-4-yl)propyl)-3-cyclohexylpropanamide

The preparation is carried out as in Example 2 with 3-cyclohexylpropanoic acid. The title compound is purified by chromatography and recrystallized from ethanol/diethyl ether.

$C_{15}H_{25}N_3O$ (379.5) M.p.: 119° C. yield: 50%

Elemental analysis: calculated: C 60.1 H 7.70 N 11.1 found: C 60.2 H 8.01 N 11.0

EXAMPLE 4

N-(3-(1H-Imidazol-4-yl)propyl)-3-cyclopentylpropanamide

The preparation is carried out as in Example 2 with 3-cyclopentylpropanoic acid. The title compound is purified by chromatography and precipitated in the hydrogenmaleate form from ethanol/diethyl ether.

$C_{14}H_{23}N_3O.C_4H_4O_4$ (365.4) M.p.: 106° C. yield: 40%

Elemental analysis: calculated: C 59.2 H 7.45 N 11.5 found: C 59.0 H 7.68 N 11.7

EXAMPLE 5

N-(3-(1H-Imidazol-4-yl)propyl)-2-(4-chlorophenoxy)acetamide

The preparation is carried out as in Example 2 with 4-chlorophenoxyacetic acid. The title compound is extracted with diethyl ether and precipitated in the hydrogenmaleate form from ethanol/diethyl ether.

$C_{14}H_{16}N_3O_2Cl.C_4H_4O_4.0.5H_2O$ (418.8) M.p.: 141° C. yield: 70%

Elemental analysis: calculated: C 51.6 H 5.05 N 10.0 found: C 51.6 H 5.15 N 10.2

EXAMPLE 6

N-(3-(1H-Imidazol-4-yl)propyl)-2-cyclohexylacetamide

The preparation is carried out as in Example 2 with cyclohexylacetic acid. The title compound is filtered under vacuum, dried and recrystallized in the hydrogenmaleate form from ethanol/diethyl ether.

$C_{14}H_{23}N_3O.C_4H_4O_4.0.5H_2O$ (374.4) M.p.: 122° C. yield: 40%

Elemental analysis: calculated: C 57.7 H 7.54 N 11.2 found: C 58.1 H 7.38 N 11.3

EXAMPLE 7

N-(3-(1H-Imidazol-4-yl)propyl)-4-cyclohexylbutanamide

The preparation is carried out as in Example 2 with 4-cyclohexylbutanoic acid. The title compound is purified by chromatography and recrystallized in the hydrogenmaleate form from ethanol/diethyl ether.

$C_{16}H_{27}N_3O.C_4H_4O_4.0.5H_2O$ (402.5) M.p.: 86° C. yield 55%

Elemental analysis: calculated: C 59.7 H 8.01 N 10.4 found: C 59.5 H 7.85 N 10.4

EXAMPLE 8

N-(3-(1H-Imidazol-4-yl)propyl)-4-methylpentanamide

The preparation is carried out as in Example 2 with 4-methylpentanoic acid. The title compound is purified by chromatography and recrystallized in the hydrogenmaleate form from ethanol/diethyl ether.

$C_{12}H_{21}N_3O.C_4H_4O_4.0.5H_2O$ (348.4) M.p.: 115° C. yield: 40%

Elemental analysis: calculated: C 55.2 H 7.52 N 12.1 found: C 55.4 H 7.57 N 12.1

EXAMPLE 9

N-(3-(1H-Imidazol-4-yl)propyl)-3,3-diphenylpropanamide

The preparation is carried out as in Example 2 with 3,3-diphenylpropanoic acid. The title compound is purified by chromatography and recrystallized in the hydrogenmaleate form from ethanol/diethyl ether.

$C_{21}H_{23}N_3O.C_4H_4O_4$ (449.5) M.p.: 116° C. yield 65%

Elemental analysis: calculated: C 66.8 H 6.05 N 9.35 found: C 66.7 H 6.03 N 9.36

EXAMPLE 10

N-(3-(1H-Imidazol-4-yl)propyl)-3-(bicyclo[2.2.1]hept-2-yl)propanamide

The preparation is carried out as in Example 2 with 3-(bicyclo[2.2.1]hept-2-yl)propanoic acid. The title compound is purified by chromatography and recrystallized in the hydrogenmaleate form from ethanol/diethyl ether.

$C_{16}H_{23}N_3O.C_4H_4O_4.0.5H_2O$ (398.5) M.p.: 112° C. yield 35%

Elemental analysis: calculated: C 60.3 H 7.08 N 10.6 found: C 60.1 H 7.46 N 10.6

EXAMPLE 11

N-(3-(1H-Imidazol-4-yl)propyl)hexamine

The preparation is carried out as in Example 2 with hexanoic acid. The title compound is purified by chromatography and recrystallized in the hydrogenmaleate form from ethanol/diethyl ether.

$C_{12}H_{21}N_3O.C_4H_4O_4.0.5H_2O$ (348.4) M.p.: 69° C. yield 45%

Elemental analysis: calculated: C 55.2 H 7.52 N 12.1 found: C 55.2 H 7.46 N 12.0

EXAMPLE 12

N-(3-(1H-Imidazol-4-yl)propyl)heptanamide

The preparation is carried out as in Example 2 with heptanoic acid. The title compound is purified by chromatography and recrystallized in the hydrogenmaleate form from ethanol/diethyl ether.

$C_{13}H_{23}N_3O.C_4H_4O_4$ (353.4) M.p.: 73°–74° C. yield 50%

Elemental analysis: calculated: C 57.8 H 7.70 N 11.9 found: C 57.5 H 8.00 N 11.8

EXAMPLE 13

N-(3-(1H-Imidazol-4-yl)propyl)octanamide

The preparation is carried out as in Example 2 with octanoic acid. The title compound is purified by chromatography and recrystallized in the hydrogenmaleate form from ethanol/diethyl ether.

$C_{14}H_{25}N_3O.C_4H_4O_4$ (367.4) M.p.: 74° C. yield 50%

Elemental analysis: calculated: C 58.8 H 7.95 N 11.4 found: C 58.6 H 8.00 N 11.3

EXAMPLE 14

N-(3-(1H-Imidazol-4-yl)propyl)-3-(2-cyclopenten-1-yl)propanamide

The preparation is carried out as in Example 2 with 3-(2-cyclopenten-1-yl)propanoic acid. The title compound is purified by chromatography and recrystallized in the hydrogenmaleate form from ethanol/diethyl ether.

$C_{14}H_{21}N_3O.C_4H_4O_4.0.5H_2O$ (372.4) M.p.: 84° C. yield 45%

Elemental analysis: calculated: C 58.1 H 7.04 N 11.3 found: C 58.2 H 6.84 N 11.7

EXAMPLE 15

(R,S)-(+)-N-(3-(1H-Imidazol-4-yl)propyl)-3-phenylbutanamide

The preparation is carried out as in Example 2 with 3-phenylbutanoic acid. The title compound is purified by chromatography and recrystallized in the hydrogenmaleate form from ethanol/diethyl ether.

$C_{16}H_{21}N_3O.C_4H_4O_4.0.25H_2O$ (391.9) M.p.: 89° C. yield 65%

Elemental analysis: calculated: C 61.3 H 6.55 N 10.7 found: C 61.3 H 6.52 N 10.8

EXAMPLE 16

N-(3-(1H-Imidazol-4-yl)propyl)-3-(2-pyrazinyl)propanamide

The preparation is carried out as in Example 2 with 3-(2-pyrazinyl)propanoic acid. The title compound is purified by chromatography and recrystallized in the hydrogenmaleate form from ethanol/diethyl ether.

$C_{13}H_{17}N_5O.2HCl.H_2O$ (350.2) M.p.: 150° C. yield 25%

Elemental analysis: calculated: C 44.6 H 6.04 N 20.0 found: C 44.9 H 5.68 N 20.3

EXAMPLE 17

N-(4-(1H-Imidazol-4-yl)butyl)-2-cyclopentylacetamide

The preparation is carried out as in Example 1 with 2-cyclopentylacetic acid and 4-(1H-imidazol-4-yl)butanamine. The title compound is extracted from water with diethyl ether and recrystallized in the hydrogenmaleate form from ethanol/diethyl ether.

$C_{14}H_{23}N_3O.C_4H_4O_4$ (374.4) M.p.: 114° C. yield 65%

Elemental analysis: calculated: C 59.2 H 7.45 N 11.5 found: C 58.8 H 7.78 N 11.5

EXAMPLE 18

N-(4-(1H-Imidazol-4-yl)butyl)-3-cyclopentylpropanamide

The preparation is carried out as in Example 17 with 3-cyclopentylpropanoic acid. The title compound is extracted from water with diethyl ether and recrystallized in the hydrogenmaleate form from ethanol/diethyl ether.

$C_{15}H_{25}N_3O.C_4H_4O_4.H_2O$ (397.5) M.p.: 124° C. yield 65%

Elemental analysis: calculated: C 57.4 H 7.86 N 10.6 found: C 57.6 H 7.48 N 10.2

EXAMPLE 19

(E)-N-(3-(1H-Imidazol-4-yl)allyl)-3-cyclopentylpropanamide

The preparation is carried out as in Example 4 with (E)-3-(1H-imidazol-4-yl)allylamine as amine component.

The title compound is extracted from water with diethyl ether and recrystallized in the hydrogenmaleate form from ethanol/diethyl ether.

$C_{14}H_{21}N_3O.C_4H_4O_4.0.5H_2O$ (372.4) M.p.: 156° C. yield 70%

Elemental analysis: calculated: C 58.1 H 7.04 N 11.3 found: C 58.1 H 6.88 N 11.3

EXAMPLE 20

N-(3-Phenylpropyl)-3-(1H-imidazol-4-yl) propanamide

The preparation is carried out as in Example 1 with 3-phenylpropanamine and 3-(1H-imidazol-4-yl)propanoic acid, the acid being here added after the reaction of the amine component with N,N'-carbonyldiimidazole. The title compound is extracted from water with diethyl ether, purified by chromatography and recrystallized in the hydrogenmaleate form from ethanol/diethyl ether.

$C_{15}H_{19}N_3O.C_4H_4O_4.0.5H_2O$ (382.4) M.p.: 116° C. yield 45%

Elemental analysis: calculated: C 59.7 H 6.33 N 11.0 found: C 59.8 H 6.09 N 10.8

EXAMPLE 21

N-(2-(1H-Imidazol-4-yl)ethyl)-4-cyclohexylbutanethioamide

First of all N-(2-(1H-imidazol-4-yl)ethyl)-4-cyclohexylbutanamide is prepared by reacting 10 mmol of 4-cyclohexylbutanoic gvbacid and 2-(1H-imidazol-4-yl) ethylamine. The compound obtained is filtered under vacuum, dried and recrystallized from ethanol/diethyl ether.

3 mmol of the latter compound are maintained for 1 h at reflux in 5 ml of phosphorus pentasulphide in 20 ml of pyridine. After evaporation under vacuum, the residue is taken up in a water/chloroform mixture, brought to a pH of 9 with aqueous ammonia and washed 3 times with water. The organic phase is concentrated and purified by chromatography. The title compound obtained is recrystallized from ethanol/diethyl ether.

$C_{15}H_{25}N_3S$ (279.5) M.p.: 82° C. yield: 50%

Elemental analysis: calculated: C 64.5 H 9.02 N 15.0 found: C 64.1 H 9.17 N 14.7

EXAMPLE 22

N-(3-(1H-Imidazol-4-yl)propyl)-3-cyclopentylpropanethioamide

The preparation is carried out as in Example 21, starting with the compound obtained in Example 4. The title compound is recrystallized in the hydrogenmaleate form from ethanol/diethyl ether.

$C_{14}H_{23}N_3S.C_4H_4O_4.H_2O$ (399.5) M.p.: 91°–92° C. yield: 25%

Elemental analysis: calculated: C 54.1 H 7.31 N 10.5 found: C 54.3 H 6.96 N 10.5

EXAMPLE 23

N-Benzyl-N'-(3-(1H-imidazol-4-yl)propyl)urea 5 mmol of 3-(1H-imidazol-4-yl)propanamine dihydrochloride and 10 mmol of triethylamine are mixed in 10 ml of acetonitrile and, after addition of 5 mmol of benzyl isocyanate, the whole mixture is brought to boiling for 1 h at reflux. After evaporation under vacuum, the title compound is taken up in a small amount of water and recrystallized in the hydrogenmaleate form from ethanol/diethyl ether.

$C_{14}H_{18}N_4O.C_4H_4O_4$ (374.4) M.p.: 119° C. yield: 80%

Elemental analysis: calculated: C 57.7 H 5.92 H 15.0 found: C 57.7 H 6.05 H 14.6

EXAMPLE 24

3-(1H-Imidazol-4-yl)propyl ester of 3-cyclopentylpropanoic acid 5 mmol of 3-(1H-imidazol-4-yl)propanol hydrochloride in 30 ml of pyridine with 10 mg of 4-dimethylaminopyridine are added to 5 mmol of the chloride of 3-cyclopentylpropanoic acid and the whole mixture is stirred for 16 h at room temperature. The solution is evaporated under vacuum, the residue is then taken up in water and extracted with diethyl ether. A hydrogenmaleate is formed from the oil obtained, decoloured with active charcoal and recrystallized from ethanol/diethyl ether.

$C_{14}H_{22}N_2O_2.C_4H_4O_4$ (366.4) M.p.: 88° C. yield: 30%

Elemental analysis: calculated: C 59.0 H 7.15 N 7.65 found: C 59.0 H 7.39 N 7.65

EXAMPLE 25

3-(1H-Imidazol-4-yl)propyl ester of benzoic acid

The preparation is carried out as in Example 24 with the chloride of benzoic acid. The title compound is crystallized in the hydrogenmaleate form from ethanol/diethyl ether.

$C_{13}H_{14}N_2O_2.C_4H_4O_4.0.5H_2O$ (355.4) M.p.: 165° C. yield: 75%

Elemental analysis: calculated: C 57.5 H 5.39 N 7.88 found: C 57.1 H 5.07 N 7.95

EXAMPLE 26

3-(1H-Imidazol-4-yl)propyl ester of 4-iodobenzoic acid

The preparation is carried out as in Example 24 with the chloride of 4-iodobenzoic acid. The title compound is crystallized in the hydrogenmaleate form from ethanol/diethyl ether.

$C_{13}H_{13}N_2O_2I.C_4H_4O_4.0.5H_2O$ (481.2) M.p.: 148° C. yield: 60%

Elemental analysis: calculated: C 42.4 H 3.77 N 5.82 found: C 42.5 H 3.52 N 5.89

EXAMPLE 27

3-(1H-Imidazol-4-yl)propyl ester of 3-iodobenzoic acid

The preparation is carried out as in Example 24 with the chloride of 3-iodobenzoic acid. The title compound is crystallized in the hydrogenmaleate form from ethanol/diethyl ether.

$C_{13}H_{13}N_2O_2I.C_4H_4O_4.0.25H_2O$ (481.2) M.p.: 105° C. yield: 70%

Elemental analysis: calculated: C 42.4 H 3.77 N 5.82 found: C 42.3 H 3.52 N 5.78

EXAMPLE 28

3-(1H-Imidazol-4-yl)propyl ester of 3-iodo-4-methylbenzoic acid

The preparation is carried out as in Example 24 with the chloride of 3-iodo-4-methylbenzoic acid. The title compound is crystallized in the hydrogenmaleate form from ethanol/diethyl ether.

$C_{14}H_{15}N_2O_2I.C_4H_4O_4$ (486.3) M.p.: 112°–133° C. yield: 70%

Elemental analysis: calculated: C 44.5 H 3.94 N 5.76 found: C 44.5 H 4.09 N 5.88

EXAMPLE 29

3-(1H-Imidazol-4-yl)propyl ester of 3-(4-iodophenyl)propanoic acid

The preparation is carried out as in Example 24 with the chloride of 3-(4-iodophenyl)propanoic acid. The title compound is crystallized in the hydrogenmaleate form from ethanol/diethyl ether.

$C_{15}H_{17}N_2O_2I.C_4O$ (500.29) M.p.: 147° C. yield: 80%

Elemental analysis: calculated: C 45.6 H 4.23 N 5.60 found: C 45.9 H 4.29 N 5.68

EXAMPLE 30

3-(1H-Imidazol-4-yl)propyl ester of 4-amino-3,5-diiodobenzoic acid

The preparation is carried out as in Example 24 with the chloride of 4-amino-3,5-diiodobenzoic acid. The title compound is crystallized in the hydrogenmaleate form from ethanol/diethyl ether.

$C_{13}H_{13}N_3O_2I_2.C_4H_4O_4$ (613.2) M.p.: 155° C. yield: 75%

Elemental analysis: calculated: C 33.3 H 2.79 N 6.85 found: C 33.1 H 2.60 N 6.83

EXAMPLE 31

3-(1H-Imidazol-4-yl)propyl ester of 4-(4-iodophenyl)butanoic acid

The preparation is carried out as in Example 24 with the chloride of 4-(4-iodophenyl)butanoic acid. The title compound is crystallized in the hydrogenmaleate form from ethanol/diethyl ether.

$C_{16}H_{19}N_2O_2I.C_4H_4O_4$ (514.3) M.p.: 126° C. yield: 80%

Elemental analysis: calculated: C 46.7 H 4.51 N 5.45 found: C 46.7 H 4.65 N 5.31

EXAMPLE 32

3-(1H-Imidazol-4-yl)propyl ester of 2-(4-iodophenyl)acetic acid

The preparation is carried out as in Example 24 with the chloride of 2-(4-iodophenyl)acetic acid. The title compound is crystallized in the hydrogenmaleate form from ethanol/diethyl ether.

$C_{14}H_{15}N_2O_2I.C_4H_4O_4$ (486.3) M.p.: 88° C. yield: 60%

Elemental analysis: calculated: C 44.5 H 3.93 N 5.76 found: C 44.7 H 3.99 N 5.55

EXAMPLE 33

3-(1H-Imidazol-4-yl)propyl ester of 4-phenylbutanoic acid

The preparation is carried out as in Example 24 with the chloride of 4-phenylbutanoic acid. The title compound is crystallized in the hydrogenmaleate form from ethanol/diethyl ether.

$C_{16}H_{20}N_2O_2.C_4H_4O_4.0.5H_2O$ (397.4) M.p.: 88° C. yield: 60%

Elemental analysis: calculated: C 60.4 H 6.34 N 7.05 found: C 60.6 H 6.19 N 7.20

EXAMPLE 34

3-(1H-Imidazol-4-yl)propyl N-benzylcarbamate

The preparation is carried out as in Example 23 with 3-(1H-imidazol-4-yl)propanol hydrochloride and 5 mmol of triethylamine. The residual oil is taken up in a small amount of water. The title compound is crystallized in the hydrogenmaleate form from ethanol/diethyl ether.

$C_{14}H_{17}N_3O.C_4H_4O_4$ (375.4) M.p.: 123° C. yield: 90%

Elemental analysis: calculated: C 57.6 H 5.64 N 11.2 found: C 57.2 H 5.63 N 11.2

EXAMPLE 35

3-(1H-Imidazol-4-yl)propyl N-(cyclohexylmethyl) carbamate

The preparation is carried out as in Example 34 with sodium 3-(1H-imidazol-4-yl)propoxide. The residual oil is taken up in a small amount of water. The title compound is filtered under vacuum, dried and recrystallized in the hydrogenmaleate form from ethanol/diethyl ether.

$C_{14}H_{23}N_3O_2.C_4H_4O_4$ (381.4) M.p.: 106° C. yield: 40%

Elemental analysis: calculated: C 56.7 H 7.13 N 11.0 found: C 56.3 H 7.33 N 11.0

EXAMPLE 36

3-Cyclohexylpropyl 3-(1H-imidazol-4-yl)propyl ether 5 mmol of sodium 3-[1-(triphenylmethyl)imidazol-4-yl] propoxide in 10 ml of toluene containing 0.5 mmol of 15-Crown-5 and 5 mmol of (3-chloropropyl)cyclohexane are mixed and the mixture is stirred for 24 h at 75° C. The suspension is concentrated under vacuum, the product obtained is dissolved in diethyl ether, the solution is filtered and the residue washed with petroleum ether (40°–60° C.). The filtrate obtained is concentrated and maintained for 1 h at the boiling point in a 2N aqueous/alcohol (ethanol/water) hydrochloric acid solution. The ethanol is removed under a low vacuum and the precipitate is filtered under vacuum. The solution is basified, extracted with dichloromethane and the organic phase is concentrated. The title compound obtained is recrystallized in the hydrogenmaleate form from ethanol/diethyl ether.

$C_{15}H_{26}N_2O.C_4H_4O_4.0.25H_2$ (370.9) M.p.: 114°–116° C. yield: 35%

Elemental analysis: calculated: C 61.52 H 8.29 N 7.55 found: C 61.60 H 8.25 N 7.50

EXAMPLE 37

3-(3,4-Difluorophenyl)propyl 3-(1H-imidazol-4-yl) propyl ether

The preparation is carried out as in Example 36 with 3-(3,4-difluorophenyl)propyl chloride. The title compound is crystallized in the hydrogenmaleate form from ethanol/diethyl ether.

$C_{15}H_{18}N_2OF_2.C_4H_4O_4$ (396.4) M.p.: 101° C. yield: 25%

Elemental analysis: calculated: C 57.6 H 5.59 N 7.07 found: C 57.4 H 5.52 N 7.14

EXAMPLE 38

3-(4-Bromophenyl)propyl 3-(1H-imidazol-4-yl) propyl ether

The preparation is carried out as in Example 36 with 3-(4-bromophenyl)propyl chloride. The title compound is crystallized in the hydrogenmaleate form from ethanol/diethyl ether.

$C_{15}H_{19}N_2OBr.C_4H_4O_4$ (439.3) M.p.: 130°–131° C. yield: 35%

Elemental analysis: calculated: C 52.0 H 5.28 N 6.38 found: C 52.4 H 5.35 N 6.57

EXAMPLE 39

3-(3-Trifluoromethylphenyl)propyl 3-(1H-imidazol-4-yl)propyl ether

The preparation is carried out as, in Example 36 with 3-(3-trifluoromethylphenyl)propyl chloride. The title compound is crystallized in the hydrogenmaleate form from ethanol/diethyl ether.

$C_{16}H_{19}N_2OF_3.C_4H_4O_4$ (428.4) M.p.: 85° C. yield: 35%

Elemental analysis: calculated: C 56.1 H 5.41 N 6.54 found: C 55.9 H 5.44 N 6.48

EXAMPLE 40

1-Naphthylmethyl 3-(1H-imidazol-4-yl)propyl ether

The preparation is carried out as in Example 36 with 1-naphthylmethyl chloride. The title compound is crystallized in the hydrogenmaleate form from ethanol/diethyl ether.

$C_{17}H_{18}N_2O.C_4H_4O_4.0.25H_2O$ (386.9) M.p.: 75° C. yield: 40%

Elemental analysis: calculated: C 65.2 H 5.86 N 7.24 found: C 65.3 H 5.71 N 6.93

EXAMPLE 41

(4-Iodophenyl)methyl 3-(1H-imidazol-4-yl)propyl ether

The preparation is carried out as in Example 36 with (4-iodophenyl)methyl chloride. The title compound is crystallized in the hydrogenmaleate form from ethanol/diethyl ether.

$C_{13}H_{15}N_2OI.C_4H_4O_4.0.5H_2O$ (467.3) M.p.: 123°–124° C. yield: 25%

Elemental analysis: calculated: C 43.7 H 4.31 N 5.99 found: C 43.6 H 3.94 N 5.99

EXAMPLE 42

4-Phenylbutyl 3-(1H-imidazol-4-yl)propyl ether

The preparation is carried out as in Example 36 with 4-phenylbutyl chloride. The title compound is crystallized in the hydrogenmaleate form from ethanol/diethyl ether.

$C_{16}H_{22}N_2O.C_4H_4O_4$ (374.4) M.p.: 96° C. yield: 40%

Elemental analysis: calculated: C 64.2 H 7.00 N 7.48 found: C 63.9 H 7.09 N 7.69

EXAMPLE 43

(Z)-N-(3-(1H-Imidazol-4-yl)allyl)-3-cyclohexylpropanamide

The preparation is carried out as in Example 3 with (Z)-3-(1H-imidazol-4-yl)allylamine. The title compound is extracted from water with diethyl ether and is precipitated in the hydrogenmaleate form from ethanol/diethyl ether.

$C_{14}H_{21}N_3O.C_4H_4O_4.0.5H_2O$ (372.4) M.p.: 134° C. yield: 65%

Elemental analysis: calculated: C 58.1 H 7.04 N 11.3 found: C 58.1 H 6.88 N 11.3

EXAMPLE 44

(R,S)-(±)-N-(3-(1H-Imidazol-4-yl)butyl)-3-cyclohexylpropanamide

The preparation is carried out as in Example 3 with (R,S)-(±)-3-(1H-imidazol-4-yl)butanamine. The title compound is extracted from water with dichloromethane and precipitated in the hydrogenmaleate form from ethanol/diethyl ether.

$C_{16}H_{27}N_3O.C_4H_4O_4.0.5H_2O$ (393.5) M.p.: 79° C. yield: 30%

Elemental analysis: calculated: C 59.7 H 8.01 N 10.4 found: C 59.8 H 7.66 N 10.5

EXAMPLE 45

3-Phenylpropyl 3-(1H-imidazol-4-yl)propyl ether

The preparation is carried out as in Example 36 with 3-phenylpropyl bromide. The title compound obtained is recrystallized in the hydrogenmaleate form from ethanol/ether.

$C_{15}H_{20}N_2O.C_4H_4O_4.0.25H_2O$ (364.9) M.p.: 103° C. yield: 40%

Elemental analysis: calculated: C 62.5 H 6.77 N 6.88 found: C 62.4 H 6.78 N 6.83

EXAMPLE 46

3-Phenylpropyl 3-(1H-imidazol-4-yl)propyl sulphide 5 mmol of 3-(1H-imidazol-4-yl)propyl chloride are introduced into a solution of 6 mmol of 3-phenylpropanethiol and 10 mmol of sodium in 30 ml of ethanol and the mixture is brought to reflux for 3 h. The suspension is evaporated under vacuum until dryness, potassium carbonate is added and the mixture is stirred in methanol/water. The residual semi-solid oil is brought to boiling in ethanol with active charcoal, filtered and recrystallized in the hydrogenmaleate form from ethanol/diethyl ether.

$C_{15}H_{20}N_2S.C_4H_4O_4.0.5H_2O$ (385.5) M.p.: 106° C. yield: 35%

Elemental analysis: calculated: C 59.2 H 6.54 N 7.27 found: C 59.3 H 6.38 N 7.30

EXAMPLE 47

4-[(4-Nitrobenzylthio)methyl]-1H-imidazole

A mixture of 1.53 g (10 mmol) of 4-chloromethylimidazole hydrochloride and 0.76 g (10 mmol) of thiourea is brought to reflux in 10 ml of ethanol for 15 min. 5 ml of ethanol, 20 ml of water and 200 mg (1.16 mmol) of 4-nitrobenzyl chloride are added and the mixture is cooled to 0°–10° C. 1.44 g (36 mmol) of a solution of sodium hydroxide in 14 ml of water are added dropwise under nitrogen at 0°–10° C., and the mixture is then stirred for 1 hour at the same temperature and for a further 3 hours at room temperature. The abovementioned is collected and washed with water to provide the title compound, M.p.: 88° C.

$C_{11}H_{11}N_3O_2S$

Elemental analysis: calculated: C 53.0 H 4.45 N 16.9 found: C 53.0 H 4.22 N 16.6

EXAMPLE 48

3-Phenylpropyl 3-(1H-imidazol-4-yl)propyl sulphoxide 0.5 g of potassium carbonate in 40 ml of dichloromethane are added to 2 mmol of the compound obtained in Example 46 and the mixture is stirred for 30 min. 2.5 mmol of chloroperbenzoic acid in 20 ml of dichloromethane are slowly added to the suspension and the mixture is stirred for 2 h at room temperature. The suspension is filtered and purification is carried out by chromatography. The title compound is recrystallized in the hydrogenmaleate form from ethanol/diethyl ether.

$C_{15}H_{20}N_2OS.C_4H_4O_4.0.5H_2O$ (401.5) M.p.: 128°–130° C. yield: 60%

Elemental analysis: calculated: C 56.8 H 6.28 N 6.98 found: C 56.8 H 6.10 N 6.88

EXAMPLE 49

1-(1H-Imidazol-4-yl)-7-phenylheptan-4-one 5 mmol of 4-(1-(triphenylmethyl)imidazol-4-yl) butanenitrile are introduced into a solution of 3-phenylpropylmagnesium bromide in 300 ml of diethyl ether and 100 ml of tetrahydrofuran and the mixture is brought to reflux for 6 h. Hydrolysis is carried out with an ammonium chloride solution, the organic phase is separated and the aqueous phase is stirred with dichloromethane. The combined and concentrated organic phases are brought to boiling point for 2 h in a 2N aqueous/alcohol (ethanol/water) hydrochloric acid solution. The ethanol is removed under vacuum, filtration is carried out and basification is carried out. The title compound is stirred in dichloromethane and recrystallized in the hydrogenmaleate form from ethanol/diethyl ether.

$C_{16}H_{20}N_2O.C_4H_4O_4.0.5H_2O$ (381.4) M.p.: 129° C. yield: 25%

Elemental analysis: calculated: C 63.0 H 6.61 N 7.34 found: C 62.6 H 6.53 N 7.86

EXAMPLE 50

1-(1H-Imidazol-4-yl)-7-phenylheptan-4-ol 1 mmol of the compound obtained in Example 49 is introduced into a suspension of 10 mmol of lithium aluminium hydride in 30 ml of diethyl ether and 10 ml of dioxane and the mixture is stirred overnight. Hydrolysis is carried out with a 2N sodium hydroxide solution and the precipitate is washed with dichloromethane. The organic phases are combined and concentrated. The title compound is recrystallized in the hydrogenmaleate form from ethanol/diethyl ether.

$C_{16}H_{22}N_2O.C_4H_4O_4.H_2O$ (392.5) M.p.: 87° C. yield: 40%

Elemental analysis: calculated: C 61.2 H 7.19 N 7.14 found: C 61.6 H 6.83 N 7.36

EXAMPLE 51

N-Cyano-N'-[3-(1H-imidazol-4-yl)propyl]-N"-cyclohexylmethylguanidine 5 mmol of diphenyl N-cyanocarbonimidate are stirred with 5 mmol of cyclohexylmethylamine in 20 ml of acetonitrile for 2 h at room temperature. 5 mmol of 3-(1H-imidazol-4-yl)propanamine are then added and the mixture is brought to reflux for 8 h. The solution is concentrated under vacuum until dryness and the residue taken up in 5% acetic acid and washed with diethyl ether. After having been basified, the solution is extracted several times with dichloromethane. The combined and concentrated organic phases are purified by chromatography. The title compound is obtained, after concentration, in the form of a dry foam from diethyl ether.

$C_{15}H_{24}N_6.0.25H_2O$ (292.9) M.p.: about 103° C. yield: 45%

Elemental analysis: calculated: C 61.5 H 8.43 N 28.7 found: C 61.5 H 8.49 N 28.3

EXAMPLE 52

N-Ethoxycarbonyl-N'-[3-(1H-imidazol-4-yl)propyl]-N"-cyclohexylmethylguanidine

The preparation is carried out as in Example 51 with diphenyl N-(ethoxycarbonyl)carbonimidate. The title compound is crystallized from diethyl ether.

$C_{17}H._{29}N_5O_2$ (335.5) M.p.: 118°–119° C. yield: 45%

Elemental analysis: calculated: C 60.9 H 8.71 N 20.9 found: C 60.7 H 8.82 N 20.5

EXAMPLE 53

N-(1,1-dimethylethoxycarbonyl)-N'-[3-(1H-imidazol-4-yl)propyl]-N"-cyclohexylmethylguanidine The preparation is carried out as in Example 51 with diphenyl N-(1,1-dimethylethoxycarbonyl)carbonimidate. The title compound is crystallized from diethyl ether.

$C_{19}H_{33}N_5O_2$ (363.5) M.p.: 137° C. yield: 55%

Elemental analysis: calculated: C 62.8 H 9.15 N 19.3 found: C 62.8 H 9.51 N 19.2

EXAMPLE 54

N-[3-(1H-Imidazol-4-yl)propyl]-N'-cyclohexylmethylguanidine 1.5 mmol of the compound obtained in Example 52 are brought to reflux for 30 min in 15 ml of 1N hydrochloric acid and are then concentrated to dryness. The residual dry form is crystallized from diethyl ether.

$C_{14}H_{25}N_5.2HCl.H_2O$ (354.3) M.p.: 76° C. yield: 95%

Elemental analysis: calculated: C 47.5 H 8.25 N 19.8 found: C 47.7 H 8.26 N 19.5

EXAMPLE 55

3-(1H-Imidazol-4-yl)propyl N-benzoylcarbamate 5 mmol of 3-(1H-imidazol-4-yl)propanol hydrochloride in 10 ml of acetonitrile are maintained at reflux for 2 h with 5 mmol of benzoyl isocyanate. After evaporation under vacuum, the title compound is stirred in water and filtered.

$C_{14}H_{15}N_3O_3.0.25H_2O$ (227.8) M.p.: 150° C. yield: 80%

Elemental analysis: calculated: C 60.5 H 5.62 N 15.1 found: C 60.4 H 5.44 N 15.2

EXAMPLE 56

3-(1H-Imidazol-4-yl)propyl N-(cyclobutylmethyl) carbamate

The preparation is carried out as in Example 23 with cyclobutylmethyl isocyanate. The title compound is extracted from water with dichloromethane and crystallized in the hydrogenmaleate form from ethanol/diethyl ether.

$C_{12}H_{19}N_3O_2.C_4H_4O_4.0.25H_2O$ (357.9) M.p.: 94° C. yield: 80%

Elemental analysis: calculated: C 53.7 H 6.62 N 11.7 found: C 53.9 H 67.2 N 11.8

EXAMPLE 57

3-(1H-Imidazol-4-yl)propyl N-(cyclopropylmethyl) carbamate

The preparation is carried out as in Example 23 with cyclopropylmethyl isocyanate. The title compound is extracted from water with dichloromethane and crystallized in the hydrogenmaleate form from ethanol/diethyl ether.

$C_{11}H_{17}N_3O_2.C_4H_4O_4.0.5H_2O$ (348.4) M.p.: 93° C. yield: 50%

Elemental analysis: calculated: C 51.7 H 6.36 N 12.1 found: C 51.8 H 6.25 N 11.9

EXAMPLE 58

3-(1H-Imidazol-4-yl)propyl (R)-(+)-N-(1-phenylethyl)carbamate

The preparation is carried out as in Example 23 with (R)-(+)-1-phenylethyl isocyanate. The title compound is extracted from water with dichloromethane, purified by chromatography and crystallized in the hydrogenmaleate form from ethanol/diethyl ether.

$C_{15}H_{19}N_3O_2.C_4H_4O_4.0.25H_2O$ (393.9) M.p.: 105° C. yield: 50%

Elemental analysis: calculated: C 57.9 H 6.01 N 10.7 found: C 57.9 H 5.88 N 10.6

EXAMPLE 59

3-(1H-Imidazol-4-yl)propyl (S)-(−)-N-(1-phenylethyl)carbamate

The preparation is carried out as in Example 23 with (S)-(−)-1-phenylethyl isocyanate. The title compound is extracted from water with dichloromethane, purified by chromatography and crystallized in the hydrogenmaleate form from ethanol/diethyl ether.

$C_{15}H_{19}N_3O_2.C_4H_4O_4.0.25H_2O$ (393.9) M.p.: 105° C. yield: 50%

Elemental analysis: calculated: C 57.9 H 6.01 N 10.7 found: C 58.1 H 6.01 N 10.7

EXAMPLE 60

3-(1H-Imidazol-4-yl)propyl N-cyclohexylcarbamate

The preparation is carried out as in Example 23 with cyclohexyl isocyanate and 5 mmol of triethylamine while leaving for 4 h at room temperature. The title compound is extracted from water with dichloromethane and crystallized in the hydrogenmaleate form from ethanol/diethyl ether.

$C_{13}H_{21}N_3O_2.C_4H_4O_4.0.25H_2O$ (371.9) M.p.: 76° C. yield: 60%

Elemental analysis: calculated: C 54.9 H 6.91 N 11.3 found: C 54.9 H 6.91 N 11.4

EXAMPLE 61

3-(1H-Imidazol-4-yl)propyl N-phenylcarbamate

The preparation is carried out as in Example 57 with phenyl isocyanate. The title compound is extracted from water with dichloromethane and crystallized in the hydrogenmaleate form from ethanol/diethyl ether.

$C_{13}H_{15}N_3O_2.C_4H_4O_4.0.25H_2O$ (365.9) M.p.: 115° C. yield: 70%

Elemental analysis: calculated: C 55.8 H 5.37 N 11.5 found: C 55.7 H 5.28 N 11.5

EXAMPLE 62

3-(1H-Imidazol-4-yl)propyl N-(4-methylphenyl) carbamate

The preparation is carried out as in Example 23 with 4-methylphenyl isocyanate. The title compound is stirred with water, filtered and crystallized in the hydrogenmaleate form from ethanol/diethyl ether.

$C_{14}H_{17}N_3O_2.C_4H_4O_4.0.25H_2O$ (379.9) M.p.: 138 140° C. yield: 85%

Elemental analysis: calculated: C 56.9 H 5.70 N 11.1 found: C 57.2 H 5.67 N 11.1

EXAMPLE 63

3-(1H-Imidazol-4-yl)propyl N-(4-trifluoromethylphenyl)carbamate

The preparation is carried out as in Example 23 with 4-trifluoromethylphenyl isocyanate. The title compound is stirred with water, filtered and crystallized in the hydrogenmaleate form from ethanol/diethyl ether.

$C_{14}H_{14}N_3O_2F_3.C_4H_4O_4.0.25H_2O$ (433.9) M.p.: 129° C. yield: 85%

Elemental analysis: calculated: C 49.8 H 4.30 N 9.69 found: C 50.0 H 4.18 N 9.74

EXAMPLE 64

3-(1H-Imidazol-4-yl)propyl N-(3-trifluoromethylphenyl)carbamate

The preparation is carried out as in Example 23 with 3-trifluoromethylphenyl isocyanate. The title compound is stirred with water, filtered and crystallized in the hydrogenmaleate form from ethanol/diethyl ether.

$C_{14}H_{14}N_3O_2F_3.C_4H_4O_4.0.25H_2O$ (433.9) M.p.: 128° C. yield: 85%

Elemental analysis: calculated: C 49.8 H 4.30 N 9.69 found: C 49.8 H 4.17 N 953

EXAMPLE 65

3-(1H-Imidazol-4-yl)propyl N-(2-trifluoromethylphenyl)carbamate

The preparation is carried out as in Example 23 with 2-trifluoromethylphenyl isocyanate. The title compound is stirred with water, filtered and crystallized in the hydrogenmaleate form from ethanol/diethyl ether.

$C_{14}H_{14}N_2O_3F_3.C_4H_4O_4.0.25H_2O$ (433.90) M.p.: 83° C. yield 85%

Elemental analysis: calculated: C 49.8 H 4.30 N 9.69 found: C 50.2 H 4.29 N 9.55

EXAMPLE 66

2-(1H-Imidazol-4-yl)ethyl N-(2-phenylethyl) carbamate

The preparation is carried out as in Example 23 with 2-phenylethyl isocyanate and 2-(1H-imidazol-4-yl)ethanol.

The title compound is extracted from water with dichloromethane, purified by chromatography and crystallized in the hydrogenmaleate form from ethanol/diethyl ether.

$C_{14}H_{17}N_3O_2.C_4H_4O_4.0.25H_2O$ (379.9) M.p.: 145° C. yield: 65%

Elemental analysis: calculated: C 56.9 H 5.70 N 11.1 found: C 56.9 H 5.63 N 10.9

EXAMPLE 67

3-(1H-Imidazol-4-yl)propyl N-(4-nitrobenzyl) carbamate

The preparation is carried out as in Example 23 with 4-nitrobenzyl isocyanate. The title compound is extracted from water with dichloromethane, purified by chromatography and crystallized in the hydrogenmaleate form from ethanol/diethyl ether.

$C_{14}H_{16}N_4O_4.C_4H_4O_4.0.25H_2O$ (424.9) M.p.: 128°–129° C. yield: 30%

Elemental analysis: calculated: C 50.9 H 4.86 N 13.2 found: C 50.9 H 4.76 N 13.2

EXAMPLE 68

3-(1H-Imidazol-4-yl)propyl N-(4-amminobenzyl) carbamate 2 mmol of the compound obtained in Example 67 are hydrogenated in 10 ml of methanol with 40 mg of palladium-on-charcoal (10%) with hydrogen. After absorption of the calculated amount of hydrogen, the solution is filtered, concentrated and purified by chromatography. The title compound obtained is crystallized in the hydrogenmaleate form from ethanol/diethyl ether.

$C_{14}H_{18}N_4O_2.C_4H_4O_4.0.25H_2O$ (394.9) M.p.: 118° C. yield: 60%

Elemental analysis: calculated: C 54.8 H 5.74 N 14.2 found: C 54.8 H 5.68 N 14.1

EXAMPLE 69

3-(1H-Imidazol-4-yl)propyl N-(3-nitrophenyl) carbamate

The preparation is carried out as in Example 23 with 3-nitrophenyl isocyanate. The title compound is extracted from water with dichloromethane, purified by chromatography and crystallized in the hydrogenmaleate form from ethanol/diethyl ether.

$C_{13}H_{14}N_4O_4.C_4H_4O_4.0.25H_2O$ (410.9) M.p.: 162° C. yield: 55%

Elemental analysis: calculated: C 49.7 H 4.54 N 13.6 found: C 49.5 H 4.37 N 13.4

EXAMPLE 70

N-[2-(1H-Imidazol-4-yl)ethyl]-N-methyl-4-cyclohexylbutanamide

The preparation is carried out, as in Example 7, with 2-(1H-imidazol-4-yl)-N-methylethylamine as amine component. The title compound is extracted from water with diethyl ether and recrystallized in the hydrogenmaleate form from ethanol/diethyl ether.

$C_6H_{27}N_3O.C_4H_4O_4.0.5H_2O$ (402.5) M.p.: 93° C. yield: 40%

Elemental analysis: calculated: C 59.68 H 8.01 N 10.44 found: C 59.57 H 7.88 N 10.50

EXAMPLE 71

3-Cyclohexylpropyl ester of 3-(1H-imidazol-4-yl) propanoic acid 5 mmol of the methyl ester of 3-(1H-imidazol-4-yl) propanoic acid are brought to reflux for 1 h in 20 ml of 3-cyclohexylpropanol while introducing HCl gas. The solution is taken up in ethyl acetate, washed with an aqueous potassium carbonate solution and concentrated. The title compound is crystallized in the hydrogenmaleate form from acetonitrile/diethyl ether.

$C_{15}H_{24}N_2O_2.C_4H_4O_4.0.5H_2O$ (389.4) M.p.: 126° C. yield: 80%

Elemental analysis: calculated: C 58.6 H 7.51 N 7.19 found: C 58.6 H 7.34 N 7.46

EXAMPLE 72

3-(1H-Imidazol-4-yl)propyl N-(2-nitrophenyl) carbamate

The preparation is carried out as in Example 23 with 2-nitrophenyl isocyanate. The title compound is separated by filtration and crystallized in the hydrogenmaleate form from ethanol/diethyl ether.

$C_{13}H_{14}N_4O_4.HCl.1.0.25H_2O$ (331.2) M.p.: 160° C. yield: 90%

Elemental analysis: calculated: C 47.1 H 4.72 N 16.9 found: C 47.0 H 4.73 N 16.7

EXAMPLE 73

3-(1H-Imidazol-4-yl)propyl N-(4-fluorophenyl) carbamate

The preparation is carried out as in Example 23 with 4-fluorophenyl isocyanate. The title compound is extracted from water with dichloromethane, purified by chromatography and crystallized in the hydrogenmaleate form from ethanol/diethyl ether.

$C_{13}H_{14}N_3O_2F.C_4H_4O_4.0.25H_2O$ (383.8) M.p.: 137° C. yield: 70%

Elemental analysis: calculated: C 53.2 H 4.86 N 11.0 found: C 53.5 H 4.76 N 11.0

EXAMPLE 74

3-(1H-Imidazol-4-yl)propyl N-(2-phenylethyl) carbamate

The preparation is carried out as in Example 23 with 2-phenylethyl isocyanate. The title compound is extracted from water with dichloromethane, purified by chromatography and crystallized in the hydrogenmaleate form from ethanol/diethyl ether.

$C_{15}H_{19}N_3O_2.C_4H_4O_4.0.25H_2O$ (393.9) M.p.: 107°–109° C. yield: 65%

Elemental analysis: calculated: C 57.9 H 6.31 N 10.7 found: C 57.8 H 6.01 N 10.7

EXAMPLE 75

3-(1H-Imidazol-4-yl)propyl N-(4-fluorobenzyl) carbamate

The preparation is carried out as in Example 23 with 4-fluorobenzyl isocyanate. The title compound is extracted from water with dichloromethane, purified by chromatography and crystallized in the hydrogenmaleate form from ethanol/diethyl ether.

$C_{14}H_{15}N_3O_2F.C_4H_4O_4.0.2H_2O$ (397.9) M.p.: 137°–138° C. yield: 60%

Elemental analysis: calculated: C 54.3 H 5.19 N 10.6 found: C 54.3 H 5.19 N 10.5

EXAMPLE 76

3-(1H-Imidazol-4-yl)propyl N-(4-chlorophenyl) carbamate

The preparation is carried out as in Example 23 with 4-chlorophenyl isocyanate. The title compound is extracted from water with dichloromethane, purified by chromatography and crystallized in the hydrogenmaleate form from ethanol/diethyl ether.

$C_{13}H_{14}N_3O_3Cl.C_4H_4O_4.0.25H_2O$ (400.3) M.p: 132° C. yield: 50%

Elemental analysis: calculated: C 51.0 H 4.66 N 10.5 found: C 51.0 H 4.51 N 10.4

EXAMPLE 77

3-(1H-Imidazol-4-yl)propyl N-(4-chlorobenzyl) carbamate

The preparation is carried out as in Example 23 with 4-chlorobenzyl isocyanate. The title compound is extracted from water with dichloromethane, purified by chromtography and crystallized in the hydrogenmaleate form from ethanol/diethyl ether.

$C_{14}H_{16}N_3O_2Cl.C_4H_4O_4.0.25H_2O$ (414.3) M.p.: 133°–134° C. yield: 60%

Elemental analysis: calculated: C 52.2 H 4.99 N 10.1 found: C 52.4 H 4.90 N 10.1

EXAMPLE 78

3-(1H-Imidazol-4-yl)propyl N-(3-iodophenyl) carbamate

The preparation is carried out as in Example 23 with 3-iodophenyl isocyanate. The title compound is extracted from water with dichloromethane, purified by chromatography and crystallized in the hydrogenmaleate form from ethanol/diethyl ether.

$C_{13}H_{14}N_3O_2I.C_4H_4O_4.0.25H_2O$ (491.8) M.p.: 132° C. yield: 60%

Elemental analysis: calculated: C 41.5 H 3.79 N 8.54 found: C 41.9 H 3.88 N 8.67

EXAMPLE 79

3-(1H-Imidazol-4-yl)propyl N-(2-iodophenyl) carbamate

The preparation is carried out as in Example 23 with 2-iodophenyl isocyanate. The title compound is extracted from water with dichloromethane, purified by chromatography and crystallized in the hydrogenmaleate form from ethanol/diethyl ether.

$C_{13}H_{14}N_3O_2I.C_4H_4O_4.0.25H_2O$ (491.8) M.p.: 114° C. yield: 50%

Elemental analysis: calculated: C 41.5 H 3.79 N 8.54 found: C 41.3 H 3.62 N 8.43

EXAMPLE 80

3-(1H-Imidazol-4-yl)propyl N-(4-iodophenyl) carbamate

The preparation is carried out as in Example 23 with 4-iodophenyl isocyanate. The title compound is extracted from water with dichloromethane, purified by chromatography and crystallized in the hydrogenmaleate form from ethanol/diethyl ether.

$C_{13}H_{14}N_3O_2I.C_4H_4O_4.0.25H_2O$ (491.8) M.p.: 139° C. yield: 55%

Elemental analysis: calculated: C 41.5 H 3.79 N 8.54 found: C 41.7 H 3.75 N 8.44

EXAMPLE 81

3-(1H-Imidazol-4-yl)propyl N-(3-phenylpropyl) carbamate

The preparation is carried out as in Example 23 with 3-phenylpropyl isocyanate. The title compound is extracted from water with dichloromethane, purified by chromatography and crystallized in the hydrogenmaleate form from ethanol/diethyl ether.

$C_{16}H_{21}N_3O_2.C_4H_4O_4.0.25H_2O$ (407.9) M.p.: 90° C. yield: 60%

Elemental analysis: calculated: C 58.9 H 6.30 N 10.3 found: C 59.1 H 6.38 N 10.5

EXAMPLE 82

3-(1H-Imidazol-4-yl)propyl N-(4-trifluoromethylbenzyl)carbamate

The preparation is carried out as in Example 23 with 4-trifluoromethylbenzyl isocyanate. The title compound is stirred with water, separated by filtration and crystallized in the hydrogenmaleate form from ethanol/diethyl ether.

$C_{15}H_{16}N_3O_2F_3.C_4H_4O_4.0.25H_2O$ (447.9) M.p.: 97° C. yield: 40%

Elemental analysis: calculated: C 51.0 H 4.61 N 9.38 found: C 51.1 H 4.45 N 9.04

EXAMPLE 83

3-(1H-Imidazol-4-yl)propyl N-benzyl-N-methylcarbamate

The preparation is carried out as in Example 23 with N-benzyl-N-methylcarbamoyl chloride. The title compound is stirred with water, separated by filtration and crystallized in the hydrogenmaleate form from ethanol/diethyl ether.

$C_{15}H_{19}N_3O_2.C_4O_4.0.25H_2O$ (393.9) M.p.: 70° C. yield: 15%

Elemental analysis: calculated: C 57.9 H 6.01 N 10.7 found: C 58.2 H 6.07 N 10.6

EXAMPLE 84

3-(1H-Imidazol-4-yl)propyl N-benzyl-N-isopropylcarbamate

The preparation is carried out as in Example 23 with N-benzyl-N-isopropylcarbamoyl chloride. The title compound is stirred with water, separated by filtration and crystallized in the hydrogenmaleate form from ethanol/diethyl ether.

$C_{17}H_{23}N_3O_2.C_4H_4O_4.0.5H_2O$ (426.5) M.p.: 74°–76° C. yield: 30%

Elemental analysis: calculated: C 59.1 H 6.62 N 9.85 found: C 59.4 H 6.54 N 9.56

EXAMPLE 85

3-(4-Chlorophenyl)propyl 3-(1H-imidazol-4-yl) propyl ether

The preparation is carried out as in Example 36 with 3-(4-chlorophenyl)propyl chloride. The title compound is crystallized in the hydrogenmaleate form from ethanol/diethyl ether.

$C_{15}H_{19}N_2OCl.C_4H_4O_4$ (394.9) M.p.: 130° C. yield: 50%

Elemental analysis: calculated: C 57.8 H 5.87 N 7.09 found: C 58.2 H 6.02 N 7.30

EXAMPLE 86

4-Chlorophenyl)methyl 3-(1H-imidazol-4-yl)propyl ether

The preparation is carried out as in Example 36 with (4-chlorophenyl)methyl chloride. The title compound is crystallized in the hydrogenmaleate form from ethanol/diethyl ether.

$C_{13}H_{15}N_2OCl.C_4H_4O_4$ (366.8) M.p.: 109° C. yield: 50%

Elemental analysis: calculated: C 55.7 H 5.22 N 7.64 found: C 55.6 H 5.44 N 7.73

EXAMPLE 87

Cyclohexylmethyl (1H-imidazol-4-yl)methyl ether

The preparation is carried out as in Example 36 with cyclohexylmethyl chloride and sodium [1-(triphenylmethyl) imidazol-4-yl]methoxide. The title compound is crystallized in the hydrogenmaleate form from ethanol/diethyl ether.

$C_{11}N_2O.C_4H_4O_4.0.25H_2O$ (314.5) M.p.: 102° C. yield: 50%

Elemental analysis: calculated: C 56.4 H 8.77 N 7.26 found: C 56.3 H 8.96 N 7.19

EXAMPLE 88

3-(4-Fluorophenyl)propyl 3-(1H-imidazol-4-yl) propyl ether

The preparation is carried out as in Example 36 with 3-(4-fluorophenyl)propyl chloride. The title compound is crystallized in the hydrogenmaleate form from ethanol/diethyl ether.

$C_{15}H_{19}N_2OF.C_4H_4O_4.0.25H_2O$ (382.9) M.p.: 118° C. yield: 45%

Elemental analysis: calculated: C 59.6 H 6.19 N 7.32 found: C 59.3 H 6.04 N 7.24

EXAMPLE 89 p-Nitrophenyl trans-3-(1H-imidazol-4-yl)-2-propenoate 2 ml (27.5 mmol) of freshly distilled thionyl chloride are added to a finely ground mixture of 1.51 g (10.8 mmol) of p-nitrophenol and 1.5 g (10.8 mmol) of trans-urocanic acid in a round-bottomed flask equipped with a drying tube containing $CaCl_2$. The mixture is progressively brought to 140° C. After 4 h, the mixture is slowly cooled to room temperature. A brown powder is extracted with $CHCl_3$/MeOH (150 ml, 2:1) while heating. The undissolved material is separated by filtration and the filtrate is treated with active charcoal. Concentration is carried out under vacuum and diethyl ether is added so as to induce precipitation of a solid (1.96 g; overall crude yield: 61%). The latter is recrystallized from MeOH and the product is washed with diethyl ether in order to remove any trace of p-nitrophenol, giving a crystalline white solid, M.p. 220°–222° C.

$C_{12}H_9N_3O_4.HCl$

Elemental analysis: calculated: C 48.7 H 3.41 N 14.2 Cl 12.0 found: C 48.4 H 3.48 N 14.2 Cl 11.9

EXAMPLE 90

2-{[2-(1H-Imidazol-4-yl)ethyl]amino}pyrimidine

A solution of 2.9 g (27 mmol) of 2-chloropyrimidine and of 3 g (27 mmol) of histamine in 30 ml of 2-propanol is brought to reflux for 36 h. The solvent is distilled under reduced pressure and the oily residue is chromatographed on a column of silica gel which is eluted with chloroform and methanol (1:1). The pure fractions are combined and evaporated until an oily residue is obtained which, treated with two equivalents of oxalic acid in absolute ethanol, provides the product in the form of an oxalate salt (monohydrate). M.p.: 200°–202° C.

$C_9H_{11}N_5.C_2H_2O_4.H_2O$

Elemental analysis: calculated: C 44.4 H 5.08 N 23.6 found: C 44.8 H 4.90 N 23.5

EXAMPLE 91

2-{[2-(1H-Imidazol-4-yl)ethyl]amino}benzothiazole

Mixing is carried out of 1.65 g (9,7 mmol) of 2-chlorobenzothiazole and 1.08 g (9.7 mmol) of histamine base in 20 ml of 2-propanol, the mixture is brought to reflux for 48 h and evaporation is carried out to dryness. The solid residue is stirred in water for 1 h and the pure product is collected by filtration; M.p. 185°–187° C. (yield 70%). The maleate salt is prepared from absolute ethanol by adding ether. After recrystallization from absolute ethanol, the maleate salt melts at 137°–138° C.

$C_{12}H_{12}N_4S.C_4H_4O_4$.

Elemental analysis: calculated: C 53.3 H 4.47 N 15.5 found: C 53.1 H 4.64 N 15.2

EXAMPLE 92

2-{[2-(1H-Imidazol-4-yl)ethyl]amino}pyridine

A solution of 2.40 g (21 mmol) of histamine base and of 3.41 g (21 mmol) of 2-bromopyridine in 5 ml of 4-picoline is brought to reflux for 26 h. The mixture is evaporated under reduced pressure and the oily residue is chromatographed on a column of silica gel, eluted with a mixture of chloroform and methanol (1%–20%). An ethanol solution of the resulting product is treated with maleic acid and then ether to give the dimaleate. The latter is recrystallized from absolute ethanol.

$C_{10}H_{12}N_4.2.2C_4H_4O_4$ M.p.: 137°–138° C.

Elemental analysis: calculated: C 49.3 H 4.59 N 12.6 found: C 49.2 H 4.76 N 12.8

EXAMPLE 93

2-{[2-(1H-Imidazol-4-yl)ethyl]amino}-3-nitropyridine 1.14 g (10.2 mmol) of histamine base and 1.62 g (10.2 mmol) of 2-chloro-3-nitropyridine are brought to reflux in 5 ml of 2-propanol for 3 h. Evaporation of the solvent under reduced pressure and purification of the solid residue by chromatography on a column of silica gel, eluted with chloroform containing increasing amounts of methanol (5, 10 and 20%), provide the title compound. M.p.: 178°–180° C. (yield 65%; ethanol:water).

$C_{10}H_{11}N_5O_2$.

Elemental analysis: calculated: C 51.5 H 4.75 N 30.0 found: C 51.6 H 4.69 N 30.0

EXAMPLE 94

2-{[2-(1H-Imidazol-4-yl)ethyl]amino}-5-nitropyridine 2.22 g (14 mmol) of 2-chloro-5-nitropyridine and an equimolar equivalent of histamine base (1.56 g) in 10 ml of 2-propanol are brought to reflux for 48 h. The reaction mixture is concentrated to dryness and the solid residue is taken up in water, heated to boiling, cooled and filtered. The filtrate is concentrated to dryness and chromatographed on a column of silica gel which is eluted with a mixture of chloroform and methanol (5, 10 and 20%). The combined pure fractions are evaporated to dryness and the solid residue is crystallized from absolute ethanol to provide the product. M.p.: 162°–163° C.

$C_{10}H_{11}N_5O_2$:

Elemental analysis: calculated: C 51.5 H 4.75 N 30.0 found: C 51.6 H 4.70 N 29.8

EXAMPLE 95

2-{[2-(1H-Imidazol-4-yl)ethyl]amino}thiazole 1.1 g (10 mmol) of histamine base and 1.6 g (10 mmol) of 2-bromothiazole are brought to reflux in 15 ml of 2-propanol for 96 h. The reaction mixture is concentrated under reduced pressure until an oily residue is obtained which is chromatographed on a column of silica gel with a mixture of chloroform and methanol (1, 5 and 20%) as eluent to provide an oil. The latter is taken up in absolute ethanol and is treated with oxalic acid (2 molar equivalents). Addition of ether gives the title compound in the dioxalate form which, after having been crystallized from 2-propanol, melts at 198°–199° C.

$C_9H_{10}N_4S.C_4H_4O_8$.

Elemental analysis: calculated: C 38.5 H 3.76 N 15.0 found: C 38.3 H 3.50 N 14.7

EXAMPLE 96

2-{[2-(1H-Imidazol-4-yl)ethyl]amino}pyrazine 1 g (8.9 mmol) of histamine and 1.03 g (8.9 mmol) of 2-chloropyrazine are brought to reflux in 20 ml of 2-propanol for 72 h, evaporated and the crude solid residue is chromatographed through silica gel, using chloroform/methanol mixtures (1%, 5%, 10% and 20% respectively). The product is converted to the dioxalate in absolute ethanol and addition of ether gives the title compound which is recrystallized from a 2-propanol/diethyl ether mixture in the form of a white solid.

M.p.: 200°–202° C.

EXAMPLE 97

2-{[2-(1H-Imidazol-4-yl)ethyl]amino}-3,6-dimethylpyrazine 1 g (8.9 mmol) of histamine and 1.28 g (8.9 mmol) of 2-chloro-3,6-dimethylpyrazine in 10 ml of 2-propanol are brought to reflux for 3 days, evaporated and the residue is chromatographed on a column of silica gel, using mixtures of chloroform and methanol (1, 10 and 20% respectively) to give the title compound in the form of an oil. The latter is converted to a monohydrated dioxalate salt which is crystallized from an isopropanol/ether (1/1) mixture. M.p.: 164°–165° C.

$C_{11}H_{15}N_5.C_4H_4O_8.H_2O$

Elemental analysis: calculated: C 43.4 H 5.09 N 16.9 found: C 43.5 H 4.97 N 16.4

EXAMPLE 98

1-{[2-(1H-Imidazol-4-yl)ethyl]amino}-4-nitrobenzene 1.45 g (13.1 mmol) of histamine and 2.06 g (13.1 mmol) of 1-chloro-4-nitrobenzene are brought to reflux in 20 ml of 2-propanol for 3 days. The cooled reaction mixture is filtered, evaporated and chromatographed on a first column of silica gel, using a chloroform/methanol (99/1) mixture, and then on a second column, using a chloroform/methanol (9/1) mixture. The pure fractions were evaporated and the resulting solid was treated with oxalic acid in ethanol. Addition of ether provided the title compound in the form of an oxalate salt, M.p.: 185°–186° C.

$C_{11}H_{12}N_4O_2.1.25C_2H_2O_4$

Elemental analysis: calculated: C 47.0 H 4.23 N 16.2 found: C 46.4 H 4.02 N 16.4

EXAMPLE 99

2-{[2-(1H-Imidazol-4-yl)ethyl]amino}-5-trifluoromethylpyridine

A solution of 1 g (8.9 mmol) of histamine base and of 1.63 g (8.9 mmol) of 2-chloro-5-trifluoromethylpyridine in 5 ml of 2-propanol was brought to reflux for 3 hwhile stirring. The cooled reaction mixture was evaporated to dryness under reduced pressure and the s6lid residue was chromatographed on a column of silica gel, using a mixture of chloroform and methanol (10/1) as eluent. Treatment of an ethanol solution of the product with a solution of oxalic acid provides the dioxalate hemihydrate which is crystallized from a 2-propanol/diethyl ether (10/1) mixture, M.p.: 174°–175° C.

$C_{11}H_{11}F_3N_4.C_4H_4O_8.0.5H_2O$

Elemental analysis: calculated: C 40.5 H 3.62 N 12.6 found: C 40.3 H 3.59 N 12.4

EXAMPLE 100

4-{[2-(1H-Imidazol-4-yl)ethyl]amino}-2-chloropyridine 38 mg (0.34 mmol) of histamine and 55 mg (0.31 mmol) of 2-chloro-4-nitropyridine N-oxide in 15 ml of 2-propanol are stirred with potassium bicarbonate at 21° C. for 3 days. The mixture is then filtered and evaporated. The resulting solid residue is chromatographed on a column of silica gel, using a chloroform/methanol (10/1) mixture. The pure fractions are evaporated under reduced pressure to give the title compound which, after crystallization from a 2-propanol/ether (1/1) mixture, melts at 164°–165° C.

$C_{10}H_{11}ClN_4.0.2H_2O$

Elemental analysis: calculated: C 53.1 H 5.07 N 24.8 Cl 15.7 found: C 53.3 H 4.84 N 24.7 Cl 16.1

EXAMPLE 101

2-{[2-(1H-Imidazol-4-yl)ethyl]amino}-5-carbomethoxypyridine 0.5 g (4.5 mmol) of histamine and 0.77 g (4.5 mmol) of 6-chloro-3-carbomethoxypyridine are stirred with potassium bicarbonate in 20 ml of tetrahydrofuran at 21° C. for 24 h and then heated at reflux for 24 h. The mixture is evaporated and the white solid residue is chromatographed through silica gel, using a chloroform/methanol (4/1) mixture as eluent. The fractions containing the pure product are combined and evaporated and the resulting oily residue is treated with a methanol solution of oxalic acid. Addition of ether provides the title compound in the form of the oxalate salt, M.p.: 209°–210° C. $C_{12}H_{14}N_4O_2.1.7C_2H_2O_4$ Elemental analysis: calculated: C 46.3 H 4.39 N 14.0 found: C 46.4 H 4.65 N 14.0

EXAMPLE 102

2-{[2-(1H-Imidazol-4-yl)ethyl]amino}-4-nitropyridine N-oxide 42 mg (0.38 mmol) of histamine and 60 mg (34 mmol) of 2-chloro-5-nitropyridine N-oxide are stirred with potassium bicarbonate in 2-propanol at 21° C. for 3 days and then evaporated. The resulting solid residue is chromatographed on a column of silica gel, using a chloroform/methanol (10/1) mixture as eluent. The fractions containing the title compound and the traces of a few impurities are subjected to preparative high performance liquid chromatography to provide the product in the form of a trifluoroacetate salt, M.p.: 193°–194° C.

EXAMPLE 103

2-{[3-(1H-Imidazol-4-yl)propyl]amino}-5-nitropyridine

A solution of 0.158 g (0.97 mmol) of 3-(1H-imidazol-4-yl)propylamine and of 0.154 g (0.97 mmol) of 2-chloro-5-nitropyridine in 10 ml of 2-propanol is brought to reflux for 21 h while stirring and evaporated under reduced pressure. The resulting residue is chromatographed on a column of silica gel, using a chloroform/methanol (1/1) mixture, to give the title compound in the form of a yellow oil. The latter is treated with oxalic acid in heated absolute ethanol to provide the oxalate salt which, after crystallization from 2-propanol, melts at 181°–182° C.

$C_{11}H_{12}N_5O_2.C_2H_2O_4$

Elemental analysis: calculated: C 46.3 H 4.48 N 20.8 found: C 46.1 H 4.17 N 20.2

EXAMPLE 104

2-{2-[(1H-Imidazol-4-yl)methylthio]ethylamino}-5-nitropyridine 3 g (22 mmol) of 4-hydroxymethyl-1H-imidazole hydrochloride and one molar equivalent of 2-aminoethanethiol (2.2 g) in 45 ml of aqueous HBr (48%) are brought to reflux for 18 h. The dark-red solution is then evaporated to dryness and the 4-[(2-aminoethyl)thiomethyl]-1H-imidazole dihydrobromide solid residue is washed with 30 ml of an absolute ethanol/ether (1/1) mixture (yield=95%), M.p.: 178°–179° C.

A solution of 5 g (15mmol) of 4-[(2-aminoethyl) thiomethyl]-1H-imidazole dihydrobromide in 5 ml of water is basified to a pH of 11 with 4.3 g (31 mmol) of $K_2CO_3$ in 15 ml of water. Extraction with 2-propanol provides the amine base which is freed of the inorganic material by subsequent washing with 2-propanol. 2 g (12.7 mmol) of the amine and 2 g (12.7 mmol) of 2-chloro-5-nitropyridine in 20 ml of 2-propanol are brought to reflux for 18 h. On leaving to stand, an orange solid settles and the latter is collected and chromatographed on a column of silica gel which is eluted with a mixture of chloroform and methanol (1, 5, 10 and 20%). The combined fractions are concentrated under reduced pressure to dryness and the resulting solid is purified by preparative reverse-phase high performance liquid chromatography. The product is crystallized from absolute ethanol to give pale-yellow crystals, M.p.: 145°–147° C.

$C_{11}H_{13}N_5O_2S$

Elemental analysis: calculated: C 47.3 H 4.69 N 25.1 found: C 46.8 H 4.51 N 24.6

EXAMPLE 105

2-{[2-(1H-Imidazol-4-yl)ethyl]amino}-5-aminopyridine 1.54 g (6.6 mmol) of 2-{[2-(1H-imidazol-4-yl)-ethyl] amino}-5-nitropyridine in 100 ml of absolute EtOH containing a few drops of acetic acid and 0.75 g of 10% palladium-on-charcoal are stirred under hydrogen (1.5 bar) at 20° C. for 4 h. The catalyst is removed and the solvent is evaporated under reduced pressure. The oxalate salt is prepared by treatment of an ethanol solution of the product obtained (title compound) with a solution of oxalic acid in EtOH followed by addition of diethyl ether. The product is recrystallized from EtOH and melts at 178°–179° C. (yield 95%).

$C_{10}H_{13}N_5.2C_2H_2O_4.H_2O$

Elemental analysis: calculated: C 41.9 H 4.77 N 17.5 found: C 41.6 H 4.57 N 17.8

EXAMPLE 106

2-[(1H-Imidazol-4-yl)methylthio]-5-nitropyridine

A mixture of 0.6 g (3.9 mmol) of 4-chloromethylimidazole and of an equimolar equivalent of thiourea (0.3 g) in 10 ml of ethanol is brought to reflux for 30 min. 5 ml of ethanol, 20 ml of water and 1.2 molar equivalents of 2-chloro-5-nitropyridine (0.74 g) in 5 ml of hot ethanol are added to this mixture. The light solution is cooled to 0°–10° C. in an ice bath and a solution of 0.49 g of sodium hydroxide in 10 ml of water is added dropwise under nitrogen at 0°–10° C. and then the mixture is stirred for a further 3 h at 21° C. The precipitate is collected, washed with water and chromatographed through silica gel with a mixture of chloroform and methanol (1–20%) to give the title compound, M.p.: 155°–156° C.

$C_9H_8N_4O_2S$ containing 2% of inorganic material

Elemental analysis: calculated: C 44.8 H 3.34 N 23.2 found: C 45.1 H 3.33 N 23.3

EXAMPLE 107

2-{2-[1H-Imidazol-4-yl]ethylthio}-5-nitropyridine

A hot solution of 0.2 g (1.3 mmol) of 2-chloro-5-nitropyridine in 5 ml of ethanol is added to a solution of 0.2 g (1.1 mmol) of S-{2-[1H-imidazol-4-yl]ethyl}isothiourea dihydrobromide in 2 ml of water. The resulting suspension is stirred under nitrogen. The reaction mixture is cooled to 0°–5° C. and a solution of 4 molar equivalents of sodium hydroxide (0.16 g) in 2 ml of water is added dropwise under $N_2$. The reaction mixture is stirred for 1 h at the same temperature and for 3 h at 21° C. The reaction mixture is evaporated to dryness and the residue is subjected to column chromatography (silica gel) eluted with a gradient mixture of chloroform and methanol (1–10%) to provide the title compound which is then crystallized from 2-propanol, M.p.: 147°–148° C.

$C_{10}H_{10}N_4O_2S.0.25H_2O$

Elemental analysis: calculated: C 47.1 H 4.15 N 22.0 S 12.6 found: C 47.4 H 3.86 N 21.5 S 12.0

EXAMPLE 108

2-{[2-(1H-Imidazol-4-yl)ethyl]thio}pyridine 0.5 g (4.4 mmol) of 4-(2-hydroxyethyl)-1H-imidazole and 0.49 g (44.4 mmol) of 2-mercaptopyridine are brought to reflux in 5 ml of 47% aqueous HBr for 24 h. The solvent is removed azeotropically with isopropanol under reduced pressure to provide the title compound in the form of a dihydrobromide monohydrate salt which, after crystallization from isopropanol, melts at 189°–190° C.

$C_{10}H_{11}N_3S.2HBr.H_2O$

Elemental analysis: calculated: C 31.2 H 3.92 N 10.9 S 8.3 found: C 31.6 H 3.87 N 11.0 S 8.6

EXAMPLE 109

2-{[2-(1H-Imidazol-4-yl)ethyl]thio}-1H-imidazole 183 mg (1.1 mmol) of 4-(2-chloroethyl)-1H-imidazole hydrochloride, 110 mg (1 mmol) of 2-mercapto-1H-imidazole and 200 mg (3.26 mmol) of solid potassium hydroxide are brought to reflux in 10ml of 2-propanol for 4 h. The mixture is then evaporated and the semi-solid residue is chromatographed through silica gel, using a chloroform/methanol (5/1) mixture. The resulting product is treated with oxalic acid in ethanol to provide the title compound in the form of an oxalate salt, M.p.: 224°–226° C.

$C_8H_{10}N_4S.1.61C_2H_2O_4$

Elemental analysis: calculated: C 39.7 H 3.92 H 16.5 S 9.45 found: C 39.5 H 3.83 N 16.5 S 9.5

EXAMPLE 110

4-[2-(4-Nitrophenoxy)ethyl]-1H-imidazole 2.09 mg (1.5 mmol) of 4-nitrophenol, 251 mg (1.4 mmol) of 4-[2-chloroethyl]-1H-imidazole hydrochloride, 475 mg (3 mmol) of potassium carbonate and sodium iodide (catalyst) are stirred at 80° C. for 5 days in 5 ml of dimethylformamide. The reaction mixture is cooled and 100 ml of diethyl ether are added. The precipitate is separated by filtration. The filtrate is evaporated under reduced pressure to give a residue which is subjected to column chromatography (using, as first eluent, chloroform and, as second eluent, a 9/10 chloroform/methanol mixture) to give the title compound which, after crystallization from methanol, melts at: 197°–200° C.

$C_{11}H_{11}N_3O_3$

Elemental analysis: calculated: C 56.7 H 4.75 N 18.0 found: C 56.9 H 4.70 N 17.9

EXAMPLE 111

4-[2-(4-Carbomethoxyphenoxy)ethyl]-1H-imidazole 228 mg (1.5 mmol) of methyl 4-hydroxybenzoate, 251 mg (1.5 mmol) of 4-[2-chloroethyl]-1H-imidazole hydrochloride, 500 mg (3.6 mmol) of potassium carbonate and sodium iodide (catalyst) are stirred at 80° C. for 3 days in 5 ml of dimethylformamide. The reaction mixture is cooled and filtered and the filtrate is evaporated under reduced pressure to give an oily residue which is subjected to column chromatography (using, as first eluent, chloroform and, as second eluent, a 95/5 chloroform/methanol mixture). The product is purified by preparative high performance liquid chromatography and crystallized from water; M.p.: 116°–118° C.

$C_{13}H_{14}N_2O_3.CF_3CO_2H.0.3H_2O$

Elemental analysis: calculated: C 49.3 H 4.30 N 7.7 found: C 49.3 H 3.92 N 7.6

EXAMPLE 112

4-[2-(4-Cyanophenoxy)ethyl]-1H-imidazole 360 mg (3 mmol) of 4-cyanophenol, 251 mg (1.5 mmol) of 4-[2-chloroethyl]imidazole hydrochloride, 500 mg (3.6 mmol) of potassium carbonate and sodium iodide (catalyst) are stirred at 80° C. for 5 days in 5 ml of dimethylformamide. The mixture is cooled and filtered. The filtrate is evaporated under reduced pressure to give an oily residue. The unreacted 4-cyanophenol is precipitated with a methanol/diethyl ether (1/10) fixture. After filtration, the filtrate is evaporated under reduced pressure to give the title compound which is crystallized from a methanol/water (10/3) mixture, M.p.: 181°–183° C.

$C_{12}H_{11}N_3O$

Elemental analysis: calculated: C 67.6 H 5.20 N 19.7 found: C 67.2 H 5.18 N 19.7

EXAMPLE 113

4-[2-(4-Acetylphenoxy)ethyl]-1H-imidazole 816 mg (6 mmol) of 4-hydroxyacetophenone, 251 mg (1.5 mmol) of 4-[2-chloroethyl]-1H-imidazole hydrochloride, 500 mg (3.6 mmol) of potassium carbonate and sodium iodide (catalyst) are stirred at 80° C. for 5 days in 5 ml of dimethylformamide. The reaction mixture is cooled, filtered and the filtrate is evaporated under reduced pressure to give an oily residue, from which 4-hydroxyacetophenone is extracted with ether at pH=1. Subsequent extraction with ethyl acetate at pH=9 gives the title compound. The latter was treated with oxalic acid in 2-propanol to give the oxalate of the title compound which is crystallized from a methanol/ether (10/1) mixture, M.p.: 178°–182° C.

$C_{13}H_{14}N_2O_2.C_2H_2O_4$

Elemental analysis: calculated: C 56.2 H 5.04 N 8.8 found: C 56.4 H 5.06 N 8.9

EXAMPLE 114

4-[2-(4-Ethoxycarbonylphenoxy)ethyl]-1H-imidazole 1.49 g (9 mmol) of ethyl 4-hydroxybenzoate, 251 mg (1.5 mmol) of 4-(2-chloroethyl)-1H-imidazole hydrochloride, 500 g (3.6 mmol) of potassium carbonate and sodium iodide (catalyst) are stirred at 80° C. for 4 days in 5 ml of dimethylformamide. The reaction mixture is cooled and then filtered. The filtrate is evaporated under reduced pressure to give an oily residue. The excess ethyl 4-hydroxybenzoate is extracted with ether at pH=1. The aqueous solution is evaporated under reduced pressure to give the title compound. The latter is purified by preparative high performance chromatography and converted to the oxalate which, after crystallization from an isopropanol/ether mixture, melts at 160°–164° C.

$C_{14}H_{16}N_2O_3.0.8C_2H_2O_4$

Elemental analysis: calculated: C 56.4 H 5.34 N 8.4 found: C 56.4 H 5.29 N 8.3

EXAMPLE 115

4-[2-(3-Nitrophenoxy)ethyl]-1H-imidazole 240 mg (60% in oil, 6 mmol) of sodium hydride are added slowly to a solution of 1.67 g (12 mmol) of 3-nitrophenol in 10 ml of dimethylformamide and the mixture is stirred at room temperature for 1 hour. 200 mg (1.2 mmol) of 4-(2-chloroethyl)-1H-imidazole hydrochloride and tetrabutylammonium iodide (catalyst) are added and the mixture is stirred at 80° C. for 3 days. The reaction mixture is cooled and 150 ml of diethyl ether are added. The precipitate is separated by filtration and the filtrate is evaporated under reduced pressure to give a residue which is purified by preparative high performance chromatography. The title compound is converted to the oxalate and crystallized from ethanol, M.p.: 174°–178° C.

$C_{11}H_{11}N_3O_3.0.75C_2H_2O_4$

Elemental analysis: calculated: C 49.9 H 4.19 N 14.0 found: C 50.1 H 4.06 N 13.8

EXAMPLE 116

4-[2-(4-Methoxyphenoxy)ethyl]-1H-imidazole 240 mg (60% in oil, 6 mmol) of sodium hydride are slowly added to a solution of 1.48 g (12 mmol) of 4-methoxyphenol in 7 ml of dimethylformamide and the mixture is stirred at room temperature for 1 hour. 200 mg (1.2 mmol) of 4-(2-chloroethyl)-1H-imidazole hydrochloride and tetrabutylammonium iodide (catalyst) are added and the mixture is stirred at 80° C. for 2 days. The reaction mixture is cooled and 150 ml of diethyl ether are added. The precipitate is separated by filtration and the filtrate is evaporated under reduced pressure to give a residue which is purified by preparative high performance chromatography. The title compound is converted to the oxalate and recrystallized from ethanol, M.p.: 178°–181° C. Elemental analysis: calculated: C 55.8 H 5.37 N 9.5 found: C 55.9 H 5.40 N 9.6

EXAMPLE 117

4-[2-(4-Propylphenoxy)ethyl]-1H-imidazole 240 mg (60% in oil; 6 mmol) of sodium hydride are slowly added to a solution of 1.63 g (12 mmol) of 4-propylphenol in 10 ml of dimethylformamide and the mixture is stirred at room temperature for 1 hour. 200 mg (1.2 mmol) of 4-(2-chloroethyl)-1H-imidazole hydrochloride and tetrabutylammonium iodide are added and the mixture is stirred at 80° C. for 3 days. The reaction mixture is cooled and 150 ml of diethyl ether are added. The precipitate is separated by filtration and the filtrate is evaporated under reduced pressure to give a residue which is purified by preparative high performance chromatography. The title compound is converted to the oxalate (from an ethanol/diethyl ether mixture), M.p.: 168°–171° C.

$C_{14}H_{18}N_2O.1.1C_2H_2O_4$

Elemental analysis: calculated: C 59.1 H 6.18 N 8.5 found: C 58.9 H 6.04 N 8.5

EXAMPLE 118

4-[2-(4-Bromophenoxy)ethyl]-1H-imidazole 240 mg (60% in oil; 6 mmol) of sodium hydride are slowly added to a solution of 2.07 g (12 mmol) of 4-bromophenol in 10 ml of formamide and the mixture is stirred at room temperature for 1 hour. 200 mg (1.2 mmol) of 4-(2-chloroethyl)-1H-imidazole hydrochloride and tetrabutylammonium iodide (catalyst) are added and the mixture is stirred at 80° C. for 3 days. The reaction mixture is cooled and 150 ml of diethyl ether are added. The precipitate is separated by filtration and the filtrate is evaporated under reduced pressure to give a residue which is subjected to column chromatography through silica gel (first eluent ethyl acetate and second eluent 95/5 ethyl acetate/methanol). The title compound is purified by preparative high performance chromatography and then converted to the oxalate which, after crystallization from an ethanol/diethyl ether mixture, melts at 162°–165° C.

$C_{11}H_{11}BrN_2O.1.1C_2H_2O_4$

Elemental analysis: calculated: C 43.3 H 3.63 N 7.7 found: C 43.2 H 3.52 N 7.7

EXAMPLE 119

4-[2-(3,5-Dichlorophenoxy)ethyl]-1H-imidazole 288 mg (60% in oil, 7.2 mmol) of sodium hydride are added to a solution of 2.34 g (14.4 mmol) of 3,5-dichlorophenol in 4 ml of dimethylformamide while cooling in an ice bath. The mixture is stirred at room temperature for 1 hour under nitrogen. 200 mg (1.20 mmol) of 4-(2-chloroethyl)-1H-imidazole hydrochloride and tetrabutylammonium iodide (catalytic amount) are then added. The mixture is heated at 80° C. for 3 days and then the solvent is evaporated under reduced pressure.

The remaining oily residue is taken up in dichloromethane and dried over anhydrous magnesium sulphate. The solvent is evaporated and the residue is chromatographed on a column of silica gel (10/1 dichloromethane/methanol) to remove the excess 3,5-dichlorophenol. The mixture of the compounds obtained after column chromatography is separated by preparative HPLC (30/70 water containing 0.1% TFA/methanol containing 0.1% TFA). The product is obtained in the trifluoroacetate form, M.p.: 115°–116° C.

$C_{11}H_{10}Cl_2N_2O.CF_3COOH$

Elemental analysis: calculated: C 42.1 H 2.99 N 7.6 found: C 42.0 H 2.76 N 7.3

EXAMPLE 120

4-[2-(2,3,4,5,6-Pentafluorophenoxy)ethyl]-1H-imidazole 240 mg (60% in oil, 6 mmol) of sodium hydride are added to a solution of 2.2 g (12 mmol) of 2,3,4,5,6-pentafluorophenol in 4 ml of dimethylformamide while cooling in an ice bath. The mixture is stirred at room temperature for 1 hour under nitrogen. 200 mg (1.2 mmol) of 4-(2-chloroethyl)-1H-imidazole hydrochloride and tetrabutylammonium iodide (catalytic amount) are then added. The mixture is heated at 80° C. for 3 days and then the solvent is evaporated under reduced pressure.

The remaining oily residue is taken up in dichloromethane and the excess 2,3,4,5,6-pentafluorophenol is extracted with an aqueous sodium bicarbonate solution. The dichloromethane is evaporated and the title compound obtained is converted to the oxalate form by treatment in isopropanol. The isopropanol is evaporated and the compound is dissolved in ethanol and treated with decolouring active charcoal. The product is obtained after filtration followed by precipitation with diethyl ether, M.p.: 163°–164° C.

$C_{11}H_7F_5N_2O.1.2C_2H_2O_4.0.2H_2O$

Elemental analysis: calculated: C 41.3 H 2.53 N 7.2 found: C 40.9 H 2.09 N 7.7

EXAMPLE 121

4-[2-(4-Trifluoromethylphenoxy)ethyl]-1H-imidazole 15 ml of freshly distilled tetrahydrofuran, 340 mg (2.1 mmol) of 4-trifluoromethylphenol and 550 mg (2.1 mmol) of triphenylphosphine are added under nitrogen to 708 g (2 mmol) of 1-triphenylmethyl-4-(2-hydroxyethyl)-1H-imidazole. The resulting mixture is cooled and stirred for 5 min. 66 mg (2.1 mmol) of diethyl azodicarboxylate in 10 ml of tetrahydrofuran are then slowly added. Stirring is continued at room temperature for 2 hours under nitrogen. The solvent is then evaporated under reduced pressure and the residue is chromatographed on a column of silica gel, using diethyl ether as the eluent, to give 1-triphenylmethyl-4-[2-(4-trifluoromethylphenoxy)ethyl]-1H-imidazole.

A solution of 640 mg (1.28 mmol) of 1-triphenylmethyl-4-[2-(4-trifluoromethylphenoxy)ethyl]-1H-imidazole in 2 ml of tetrahydrofuran and 5 ml of 2N hydrochloric acid is heated at 70° C. for 2 hours. The tetrahydrofuran is then evaporated under reduced pressure and the residue extracted with diethyl ether. The aqueous solution is basified with potassium carbonate and the white solid is filtered and washed 3 times with water to give the title compound, M.p.: 105°–109° C.

$C_{12}H_{11}N_2OF_3$

Elemental analysis: calculated: C 56.25 H 4.33 N 10.93 found: C 56.30 H 4.33 N 10.67

EXAMPLE 122

4-[2-(4-Ethylphenoxy)ethyl]-1H-imidazole 180 mg (60% in oil; 4.5 mmol) of sodium hydride are slowly added to a solution of 1.1 g (9 mmol) of 4-ethylphenol in 7 ml of dimethylformamide and the mixture is stirred at room temperature for 2 hours. 150 mg (0.9 mmol) of 4-(2-chloroethyl)-1H-imidazole hydrochloride and tetrabutylammonium iodide (catalyst) are added and the mixture is stirred at 80° C. for 3 days. The solvent is concentrated and 50 ml of diethyl ether are added. The precipitate is separated by filtration and the filtrate is evaporated under reduced pressure to give a residue which is subjected to column chromatography through silica gel (first eluent ethyl acetate, second eluent 95/5 ethyl acetate/methanol). The title compound is then purified by preparative chromatography and then converted to the oxalate which, after crystallization from an ethanol/diethyl ether mixture, melts at 178° C.

$C_{13}H_{16}N_2O.0.85C_2H_2O_4$

Elemental analysis: calculated: C 60.3 H 6.09 N 9.6 found: C 60.3 H 6.00 N 9.6

EXAMPLE 123

4-[2-(3-Cyanophenoxy)ethyl]-1H-imidazole 240 mg (60% in oil; 6 mmol) of sodium hydride are added to a solution of 1.43 g (12 mmol) of 3-hydroxybenzonitrile in 10 ml of dimethylformamide and the mixture is stirred at room temperature for 1 hour under nitrogen. 200 mg (1.2 mmol) of 4-(2-chloroethyl)-1H-imidazole hydrochloride and tetrabutylammonium iodide (catalytic amount) are added and the mixture is heated for 3 hours at 80° C. The solvent is evaporated under reduced pressure and the oily residue is stirred in ethanol and filtered. The filtrate is evaporated and the residue is purified by chromatography on a column of silica gel (first eluent chloroform, second eluent 95/5 chloroform/methanol). The title compound is converted to the oxalate and crystallized from a 2/1 ethanol/diethyl ether mixture, M.p.: 189°–190° C.

$C_{12}H_{11}N_3O.C_2H_2O_4$

Elemental analysis: calculated: C 55.5 H 4.32 N 13.9 found: C 55.4 H 4.18 N 13.8

EXAMPLE 124

4-[2-(2-Cyanophenoxy)ethyl]-1H-imidazole 240 mg (60% in oil; 6 mmol) of sodium hydride are added to a solution of 1.43 g (12 mmol) of 2-hydroxybenzonitrile in 10 ml of dimethylformamide. The mixture is stirred at room temperature for 1 hour under nitrogen. 200 mg (1.2 mmol) of 4-(2-chloroethyl)-1H-imidazole hydrochloride and tetrabutylammonium iodide (catalytic amount) are added and the mixture is heated at 80° C. for 3 days. The solvent is evaporated under reduced pressure and the oily residue is stirred in ethanol and filtered. The filtrate is evaporated and the residue subjected to chromatography on a column of silica gel (first eluent chloroform, second eluent 95/5 chloroform/methanol). The title compound is converted to the oxalate and crystallized from an ethanol/diethyl ether (2/1) mixture, M.p.: 170°–171° C.

$C_{12}H_{11}N_3O.0.95C_2H_2O_4$ $C_{12}H_{11}N_3O.0.95C_2H_2O_4$

Elemental analysis: calculated: C 55.9 H 4.35 N 14.1 found: C 56.1 H 4.25 N 14.1

EXAMPLE 125

4-[2-(2-Naphthyloxy)ethyl]-1H-imidazole 240 mg (60% in oil, 6 mmol) of sodium hydride are added to a solution of 1.73 g (12 mmol) of 2-naphthol in 10 ml of dimethylformamide. The mixture is stirred at room temperature for 3 hours under nitrogen. 200 mg (1.2 mmol) of 4-(2-chloroethyl)-1H-imidazole hydrochloride and tetrabutylammonium iodide (catalytic amount) are added and the mixture is heated at 100° C. for 3 days and then the solvent is evaporated under reduced pressure. The excess 2-naphthol is extracted with diethyl ether under acidic conditions (dilute hydrochloric acid). The aqueous solution is basified with potassium carbonate and the product is extracted with diethyl ether. The ethereal extracts are concentrated and the residue obtained is crystallized from a methanol/water (½) mixture, M.p.: 157°–158° C.

$C_{15}H_{14}N_2O.0.1H_2O$

Elemental analysis: calculated: C 75.0 H 5.96 N 11.7 found: C 75.0 H 5.79 N 11.7

EXAMPLE 126

4-[2-(1-Naphthyloxy)ethyl]-1H-imidazole 240 mg (60% in oil, 6 mmol) of sodium hydride are added to a solution of 1.73 g (12 mmol) of 1-naphthol in 10 ml of dimethylformamide. The mixture is stirred at room temperature for 1 hour under nitrogen. 200 mg (1.2 mmol) of 4-(2-chloroethyl)-1H-imidazole hydrochloride and tetrabutylammonium iodide (catalytic amount) are added. The mixture is heated at 100° C. for 3 days and the solvent is then evaporated under reduced pressure. The remaining oily residue is taken up in dichloromethane and an aqueous sodium carbonate solution and treated with active charcoal. The dichloromethane solution is separated and evaporated and the remaining residue is chromatographed on a column of silica gel (10/1 dichloromethane/methanol) to give the title compound in the base form. The oxalate is prepared from isopropanol and is crystallized from ethanol, M.p.: 187°–189° C.

$C_{15}H_{14}N_2O.1.75C_2H_2O_4$

Elemental analysis: calculated: C 64.8 H 5.11 N 9.2 found: C 64.8 H 4.76 N 8.9

EXAMPLE 127

4-[2-(4-Benzoylphenoxy)ethyl]-1H-imidazole 240 mg (60% in oil, 6 mmol) of sodium hydride are added to a solution of 2.34 g (12 mmol) of 4-hydroxybenzophenone in 10 ml of dimethylformamide. The mixture is stirred at room temperature for 1 hour under nitrogen. 200 mg (1.2 mmol) of 4-(2-chloroethyl)-1H-imidazole hydrochloride and tetrabutylammonium iodide (catalytic amount) are then added. The mixture is heated at 100° C. for 2 days and the solvent is then evaporated under reduced pressure. Dilute hydrochloric acid is added to the oily residue and the excess hydroxybenzophenone is extracted with diethyl ether. The aqueous solution is basified with potassium carbonate and the product is extracted with diethyl ether. The title compound is converted to the dioxalate. Crystallization from an ethanol/diethyl ether (2/1) mixture gives a pure product, M.p.: 193°–194° C.

$C_{18}H_{16}N_2O_2.1.3C_2H_2O_4$

Elemental analysis: calculated: C 60.4 H 4.58 N 6.8 found: C 60.2 H 4.63 N 7.1

EXAMPLE 128

4-[2-(4-Nitrophenylthio)ethyl]-1H-imidazole 200 mg (60% in oil, 5 mmol) of sodium hydride are added to a solution of 1.86 g (12 mmol) of 4-nitrothiophenol in 10 ml of dimethylformamide. The mixture is stirred at room temperature for 1 hour under nitrogen. 200 g (1.2 mmol) of 4-(2-chloroethyl)-1H-imidazole hydrochloride and tetrabutylammonium iodide (catalytic amount) are then added. The mixture is heated for 1 day at 80° C. and then the solvent is evaporated under reduced pressure. The residue is stirred in diethyl ether and filtered. Dilute hydrochloric acid is added to the filtrate and the excess 4-nitrothiophenol is removed by extracting with diethyl ether. The aqueous solution is basified with potassium carbonate and then the title compound is extracted with chloroform and crystallized from ethanol, M.p.: 167°–168° C.

$C_{11}H_{11}N_3O_2S$

Elemental analysis: calculated: C 53.0 H 4.45 N 16.9 found: C 53.1 H 4.41 N 16.8

EXAMPLE 129

4-[3-(4-Fluorophenoxy)propyl]-1H-imidazole 5 ml of freshly distilled tetrahydrofuran, 120 mg (1 mmol) of 4-fluorophenol and 270 mg (1 mmol) of triphenylphosphine are added, under nitrogen, to 368 mg (1 mmol) of 1-triphenylmethyl-4-(3-hydroxypropyl)-1H-imidazole. The resulting mixture is cooled and stirred for 5 min. 180 mg (1 mmol) of diethyl azodicarboxylate in 5 ml of tetrahydrofuran are then slowly added. Stirring is continued at room temperature for 3 days under nitrogen. The solvent is then evaporated under reduced pressure and the residue is subjected to chromatography on a column of silica gel, using diethyl ether as eluent, to give 1-triphenylmethyl-4-[3-(4-fluorophenoxy)propyl]-1H-imidazole.

A solution of 147 mg (0.4 mmol) of 1-triphenylmethyl-4-[3-(4-fluorophenoxy)propyl]-1H-imidazole in 1 ml of tetrahydrofuran and 2 ml of 2N hydrochloric acid is heated at 70° C. for 2 hours. The tetrahydrofuran is then evaporated under reduced pressure. The aqueous solution is filtered and basified with potassium bicarbonate. The product is extracted with chloroform and dried over magnesium sulphate. The solvent is evaporated under reduced pressure to give the title compound in the form of a white solid, M.p.: 135°–137° C.

$C_{12}H_{13}N_2OF.0.07CHCl_3$

Elemental analysis: calculated: C 63.4 H 5.76 N 12.25 found: C 63.3 H 5.66 N 12.33

EXAMPLE 130

4-[3-(4-Cyanophenoxy)propyl]-1H-imidazole (a) 1-Triphenylmethyl-4-(3-hydroxypropyl)-1H-imidazole A solution of 2.0 g (15.85 mmol) of 4-(3-hydroxypropyl)-1H-imidazole and 5.5 ml (54.3 mmol) of dry ethylamine in 15.6 ml of dimethylformamide is treated with 4.86 g (17.4 mmol) of triphenylmethyl chloride in 5 ml of dimethylformamide under nitrogen. The mixture obtained is stirred at room temperature for 2 hours and is then poured onto 350 g of crushed ice. The resulting solid is collected by filtration, washed three times with water and purified on a chromatographic column using, as eluent, chloroform and then a chloroform/methanol (1/1) mixture to give 1-triphenylmethyl-4-(3-hydroxypropyl)-1H-imidazole, M.p.: 132°–133° C.

(b) 5 ml of freshly distilled tetrahydrofuran and 71 mg (0.6 mmol) of triphenylphosphine are added, under nitrogen, to 184 mg (0.5 mmol) of 1-triphenylmethyl-4-(3-hydroxypropyl)-1H-imidazole. The resulting mixture is cooled and stirred for 5 min. 104 mg (0.6 mmol) of diethyl azodicarboxylate in 3 ml of tetrahydrofuran are then slowly added and stirring is continued at room temperature for 3 hours under nitrogen. The solvent is then evaporated under reduced pressure and the residue is chromatographed on a column of silica gel (first eluent petroleum ether/diethyl ether (1/1); second eluent diethyl ether) to give 1-triphenylmethyl-4-[3-(4-cyanophenoxy)propyl]-1H-imidazole, .M.p.: 187°–188° C.

$C_{12}H_{27}N_3O.0.3H_2O$

Elemental analysis: calculated: C 81.5 H 5.82 N 8.9 found: C 81.2 H 5.41 N 8.8

(c) A solution of 96 mg (0.2 mmol) of 1-triphenylmethyl-4-[3-(4-cyanophenoxy)propyl]-1H-imidazole in 2 ml of tetrahydrofuran and 5 ml of 2N hydrochloric acid is heated at 70° C. for 6 hours. The tetrahydrofuran is then evaporated under reduced pressure and the residue extracted with diethyl ether. The aqueous solution is basified with potassium carbonate and the product is extracted with chloroform and dried over magnesium sulphate. The solvent is then evaporated under reduced pressure to give the title compound in the form of a white solid which is crystallized from an ethanol/ether (1/2) mixture, M.p.: 194°–195° C.

$C_{13}H_{13}N_3O.0.1H_2O$

Elemental analysis: calculated: C 68.2 H 5.81 N 18.3 found: C 68.3 H 5.51 N 18.1

EXAMPLE 131

4-[3-(4-Trifluoromethylphenoxy)propyl]-1H-imidazole (a) 5 ml of tetrahydrofuran, 129 mg (0.8 mmol) of 4-trifluoromethylphenol and 209 mg (0.8mmol) of triphenylphosphine are added, under nitrogen, to 280 mg (0.76 mmol) of 1-triphenylmethyl-4-(3-hydroxypropyl)-1H-imidazole. The resulting mixture is stirred for 5 min. 139 mg (0.8 mmol) of diethyl azodicarboxylate in 5 ml of tetrahydrofuran are then slowly added. Stirring is continued at room temperature for 3 hours under nitrogen. The solvent is then evaporated and the residue is then chromatographed on a column of silica gel (first eluent petroleum ether containing increasing amounts of diethyl ether up to 100%) to give the monohydrate of 1-triphenylmethyl-4-[3-(4-trifluoromethylphenoxy)propyl]-1H-imidazole which is crystallized from ethanol, M.p.: 150°–151° C.

$C_{32}H_{27}FN_2O.1.1H_2O$

Elemental analysis: calculated: C 72.2 H 5.33 N 5.3 found: C 72.1 H 5.44 N 5.2

(b) A solution of 260 mg (0.5 mmol) of 1-triphenylmethyl-4-[3-(4-trifluoromethylphenoxy)propyl]-1H-imidazole in 2 ml of tetrahydrofuran and 5 ml of 2N hydrochloric acid is heated at 70° C. for 6 hours. The organic solvent is then evaporated under reduced pressure and the resulting residue is washed with diethyl ether. The aqueous solution is basified with potassium carbonate and the title compound is extracted with diethyl ether. The extract is dried over magnesium sulphate and the solvent is evaporated under reduced pressure to give the title compound in the form of a white solid. The latter is converted into the oxalate which is crystallized from an ethanol/diethyl ether mixture, M.p.: 201°–204° C.

$C_{13}H_{13}F_3N_2O.1.1C_2H_2O_4$

Elemental analysis: calculated: C 49.4 H 4.15 N 7.6 found: C 49.7 H 3.79 N 7.5

The compounds of the preceding examples are collated in the following Table I.

TABLE I

| Example | Chain A | X | Chain B | Y |
|---|---|---|---|---|
| 1 | $CH_2$ | NHCO | $(CH_2)_4$ | 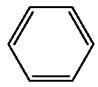 |
| 2 | $(CH_2)_3$ | NHCO | $(CH_2)_2$ | 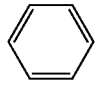 |
| 3 | $(CH_2)_3$ | NHCO | $(CH_2)_2$ | 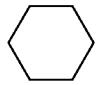 |
| 4 | $(CH_2)_3$ | NHCO | $(CH_2)_2$ | 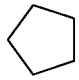 |
| 5 | $(CH_2)_3$ | NHCO | $CH_2O$ | 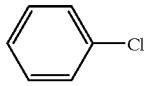 |
| 6 | $(CH_2)_3$ | NHCO | $CH_2$ | 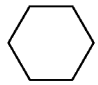 |
| 7 | $(CH_2)_3$ | NHCO | $(CH_2)_3$ | 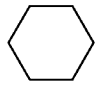 |
| 8 | $(CH_2)_3$ | NHCO | $(CH_2)_2$ | 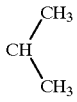 |
| 9 | $(CH_2)_3$ | NHCO | $CH_2$—CH | 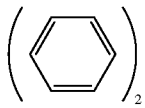 |
| 10 | $(CH_2)_3$ | NHCO | $(CH_2)_2$ | 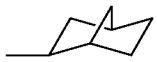 |
| 11 | $(CH_2)_3$ | NHCO | $(CH_2)_2$ | $(CH_2)_2$—$CH_3$ |
| 12 | $(CH_2)_3$ | NHCO | $(CH_2)_2$ | $(CH_2)_3$—$CH_3$ |
| 13 | $(CH_2)_3$ | NHCO | $(CH_2)_2$ | $(CH_2)_4$—$CH_3$ |

TABLE I-continued

| Example | Chain A | X | Chain B | Y |
|---|---|---|---|---|
| 14 | $(CH_2)_3$ | NHCO | $(CH_2)_2$ | |
| 15 | $(CH_2)_3$ | NHCO | $CH_2$—$CH(CH_3)$ | |
| 16 | $(CH_2)_3$ | NHCO | $(CH_2)_2$ | |
| 17 | $(CH_2)_4$ | NHCO | $CH_2$ | |
| 18 | $(CH_2)_4$ | NHCO | $(CH_2)_2$ | |
| 19 | | NHCO | $(CH_2)_2$ | |
| 20 | $(CH_2)_2$ | CONH | $(CH_2)_3$ | |
| 21 | $(CH_2)_3$ | NHCS | $(CH_2)_3$ | |
| 22 | $(CH_2)_3$ | NHCS | $(CH_2)_3$ | |
| 23 | $(CH_2)_3$ | NHCONH | $CH_2$ | |
| 24 | $(CH_2)_3$ | O—CO | $(CH_2)_2$ | |
| 25 | $(CH_2)_3$ | O—CO | — | |
| 26 | $(CH_2)_3$ | O—CO | — | |

TABLE I-continued
| Example | Chain A | X | Chain B | Y |
|---|---|---|---|---|
| 27 | $(CH_2)_3$ | O—CO | — | 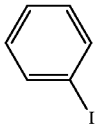 |
| 28 | $(CH_2)_3$ | O—CO | — | 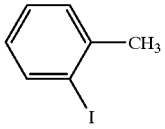 |
| 29 | $(CH_2)_3$ | O—CO | $(CH_2)_2$ | 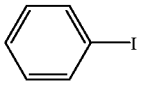 |
| 30 | $(CH_2)_3$ | O—CO | — | 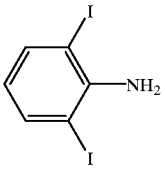 |
| 31 | $(CH_2)_3$ | O—CO | $(CH_2)_3$ | 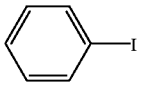 |
| 32 | $(CH_2)_3$ | O—CO | $CH_2$ | 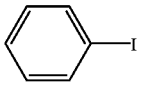 |
| 33 | $(CH_2)_3$ | O—CO | $(CH_2)_3$ | 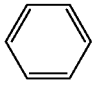 |
| 34 | $(CH_2)_3$ | OCONH | $CH_2$ | 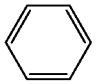 |
| 35 | $(CH_2)_3$ | OCONH | $CH_2$ | 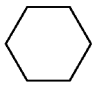 |
| 36 | $(CH_2)_3$ | O | $(CH_2)_3$ | 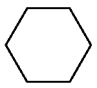 |
| 37 | $(CH_2)_3$ | O | $(CH_2)_3$ | 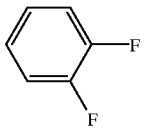 |
| 38 | $(CH_2)_3$ | O | $(CH_2)_3$ | 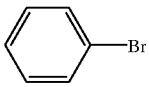 |

TABLE I-continued
| Example | Chain A | X | Chain B | Y |
|---|---|---|---|---|
| 39 | $(CH_2)_3$ | O | $(CH_2)_3$ | 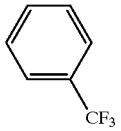 |
| 40 | $(CH_2)_3$ | O | $CH_2$ | 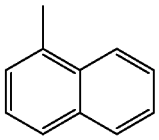 |
| 41 | $(CH_2)_3$ | O | $CH_2$ | 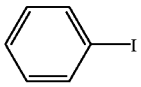 |
| 42 | $(CH_2)_3$ | O | $(CH_2)_4$ | 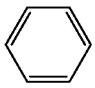 |
| 43 | 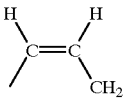 | NHCO | $(CH_2)_2$ | 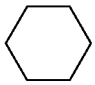 |
| 44 | 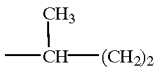 | NHCO | $(CH_2)_2$ | 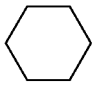 |
| 45 | $(CH_2)_3$ | O | $(CH_2)_3$ | 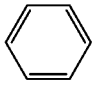 |
| 46 | $(CH_2)_3$ | S | $(CH_2)_3$ | 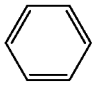 |
| 47 | $CH_2$ | S | $CH_2$ | 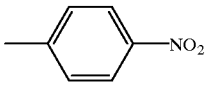 |
| 48 | $(CH_2)_3$ | 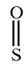 | $(CH_2)_3$ | 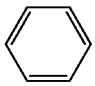 |
| 49 | $(CH_2)_3$ | 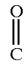 | $(CH_2)_3$ | 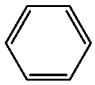 |
| 50 | $(CH_2)_3$ | 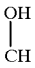 | $(CH_2)_3$ | 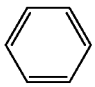 |
| 51 | $(CH_2)_3$ | 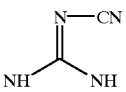 | $CH_2$ | 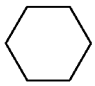 |

TABLE I-continued
| Example | Chain A | X | Chain B | Y |
|---|---|---|---|---|
| 52 | $(CH_2)_3$ | 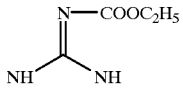 | $CH_2$ | 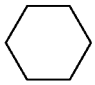 |
| 53 | $(CH_2)_3$ | 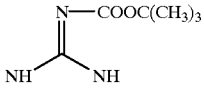 | $CH_2$ | 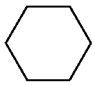 |
| 54 | $(CH_2)_3$ | 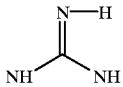 | $CH_2$ | 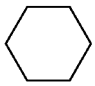 |
| 55 | $(CH_2)_3$ | 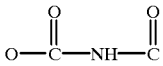 | — | 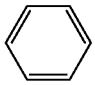 |
| 56 | $(CH_2)_3$ | 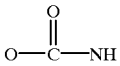 | $CH_2$ | 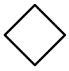 |
| 57 | $(CH_2)_3$ | 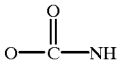 | $CH_2$ | 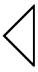 |
| 58 | $(CH_2)_3$ | 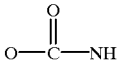 | 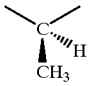 | 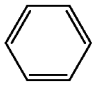 |
| 59 | $(CH_2)_3$ | 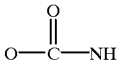 | 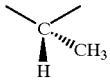 | 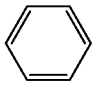 |
| 60 | $(CH_2)_3$ | 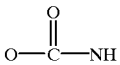 | — | 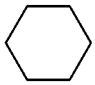 |
| 61 | $(CH_2)_3$ | 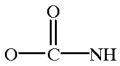 | — | 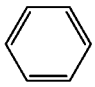 |
| 62 | $(CH_2)_3$ | 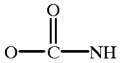 | — | 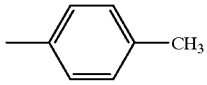 |
| 63 | $(CH_2)_3$ | 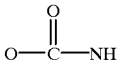 | — | 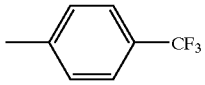 |
| 64 | $(CH_2)_3$ | 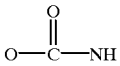 | — | 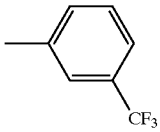 |

TABLE I-continued
| Example | Chain A | X | Chain B | Y |
|---|---|---|---|---|
| 65 | $(CH_2)_3$ | O—C(=O)—NH | — | 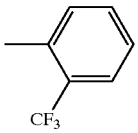 |
| 66 | $(CH_2)_2$ | O—C(=O)—NH | $(CH_2)_2$ | 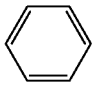 |
| 67 | $(CH_2)_3$ | O—C(=O)—NH | $CH_2$ | 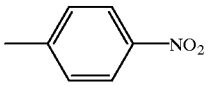 |
| 68 | $(CH_2)_3$ | O—C(=O)—NH | $CH_2$ | 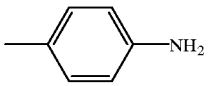 |
| 69 | $(CH_2)_3$ | O—C(=O)—NH | — | 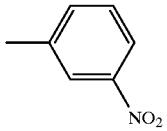 |
| 70 | $(CH_2)_2$ | 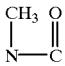 | $(CH_2)_3$ | 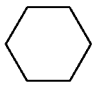 |
| 71 | $(CH_2)_2$ | COO | $(CH_2)_3$ | 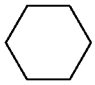 |
| 72 | $(CH_2)_3$ | O—C(=O)—NH | — | 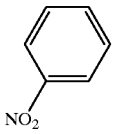 |
| 73 | $(CH_2)_3$ | O—C(=O)—NH | — | 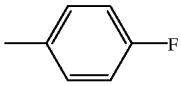 |
| 74 | $(CH_2)_3$ | O—C(=O)—NH | $(CH_2)_2$ | 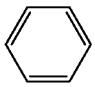 |
| 75 | $(CH_2)_3$ | O—C(=O)—NH | $CH_2$ | 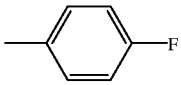 |
| 76 | $(CH_2)_3$ | O—C(=O)—NH | — | 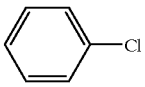 |
| 77 | $(CH_2)_3$ | O—C(=O)—NH | $CH_2$ | 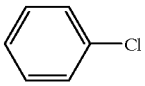 |

TABLE I-continued
| Example | Chain A | X | Chain B | Y |
|---|---|---|---|---|
| 78 | $(CH_2)_3$ | O—C(=O)—NH | — | 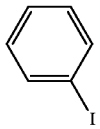 |
| 79 | $(CH_2)_3$ | O—C(=O)—NH | — | 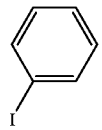 |
| 80 | $(CH_2)_3$ | O—C(=O)—NH | — | 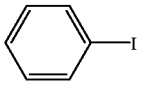 |
| 81 | $(CH_2)_3$ | O—C(=O)—NH | $(CH_2)_3$ | 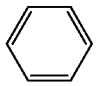 |
| 82 | $(CH_2)_3$ | O—C(=O)—NH | $CH_2$ | 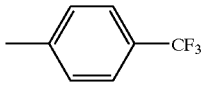 |
| 83 | $(CH_2)_3$ | O—C(=O)—N(CH$_3$) | $CH_2$ | 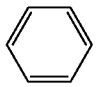 |
| 84 | $(CH_2)_3$ | O—C(=O)—N(CH(CH$_3$)$_2$) | $CH_2$ | 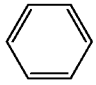 |
| 85 | $(CH_2)_3$ | O | $(CH_2)_3$ | 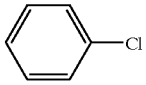 |
| 86 | $(CH_2)_3$ | O | $CH_2$ | 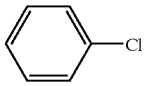 |
| 87 | $CH_2$ | O | $CH_2$ | 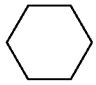 |
| 88 | $(CH_2)_3$ | O | $(CH_2)_3$ | 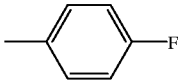 |
| 89 | CH=CH | CO—O | — | 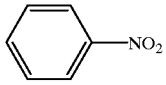 |
| 90 | $(CH_2)_2$ | NH | — | 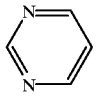 |

TABLE I-continued
| Example | Chain A | X | Chain B | Y |
|---|---|---|---|---|
| 91 | $(CH_2)_2$ | NH | — | 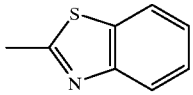 |
| 92 | $(CH_2)_2$ | NH | — | 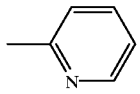 |
| 93 | $(CH_2)_2$ | NH | — | 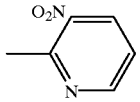 |
| 94 | $(CH_2)_2$ | NH | — | 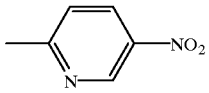 |
| 95 | $(CH_2)_2$ | NH | — | 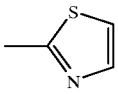 |
| 96 | $(CH_2)_2$ | NH | — | 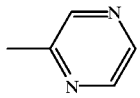 |
| 97 | $(CH_2)_2$ | NH | — | 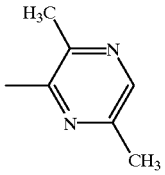 |
| 98 | $(CH_2)_2$ | NH | — | 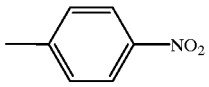 |
| 99 | $(CH_2)_2$ | NH | — | 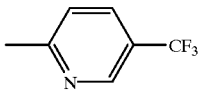 |
| 100 | $(CH_2)_2$ | NH | — | 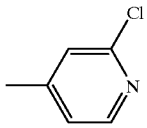 |
| 101 | $(CH_2)_2$ | NH | — | 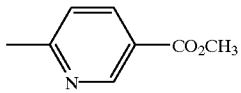 |
| 102 | $(CH_2)_2$ | NH | — | 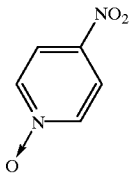 |

TABLE I-continued
| Example | Chain A | X | Chain B | Y |
|---|---|---|---|---|
| 103 | $(CH_2)_3$ | NH | — | 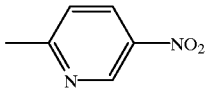 |
| 104 | $CH_2SCH_2CH_2$ | NH | — | 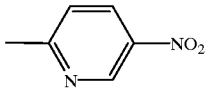 |
| 105 | $(CH_2)_2$ | NH | — | 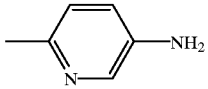 |
| 106 | $CH_2$ | S | — | 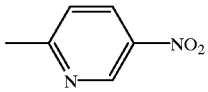 |
| 107 | $(CH_2)_2$ | S | — | 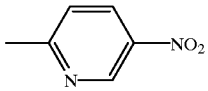 |
| 108 | $(CH_2)_2$ | S | — | 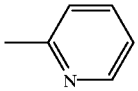 |
| 109 | $(CH_2)_2$ | S | — | 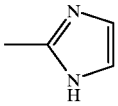 |
| 110 | $(CH_2)_2$ | O | — | 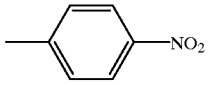 |
| 111 | $(CH_2)_2$ | O | — | 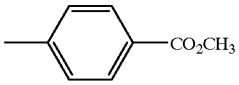 |
| 112 | $(CH_2)_2$ | O | — | 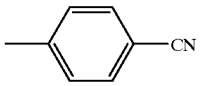 |
| 113 | $(CH_2)_2$ | O | — | 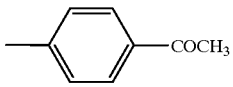 |
| 114 | $(CH_2)_2$ | O | — | 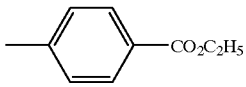 |
| 115 | $(CH_2)_2$ | O | — | 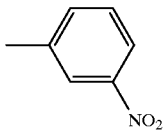 |

TABLE I-continued
| Example | Chain A | X | Chain B | Y |
|---|---|---|---|---|
| 116 | $(CH_2)_2$ | O | — | 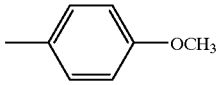 |
| 117 | $(CH_2)_2$ | O | — | 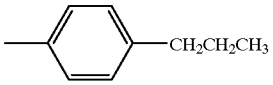 |
| 118 | $(CH_2)_3$ | O | — | 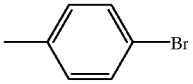 |
| 119 | $(CH_2)_2$ | O | — | 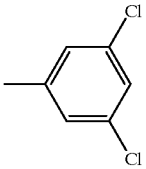 |
| 120 | $(CH_2)_2$ | O | — | 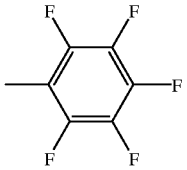 |
| 121 | $(CH_2)_2$ | O | — | 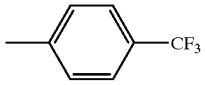 |
| 122 | $(CH_2)_2$ | O | — | 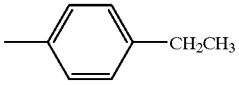 |
| 123 | $(CH_2)_3$ | O | — | 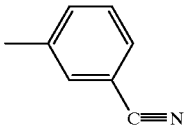 |
| 124 | $(CH_2)_2$ | O | — | 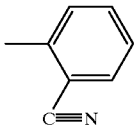 |
| 125 | $(CH_2)_2$ | O | — | 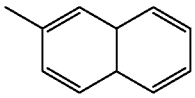 |
| 126 | $(CH_2)_2$ | O | — | 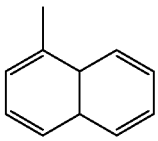 |

TABLE I-continued

| Example | Chain A | X | Chain B | Y |
|---|---|---|---|---|
| 127 | $(CH_2)_2$ | O | — | 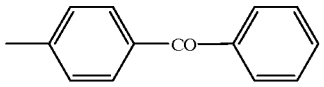 |
| 128 | $(CH_2)_2$ | S | — | 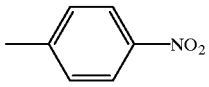 |
| 129 | $(CH_2)_3$ | O | — | 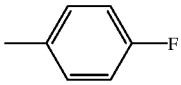 |
| 130 | $(CH_2)_3$ | O | — | 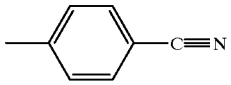 |
| 131 | $(CH_2)_3$ | O | — | 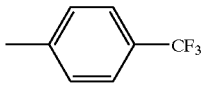 |

PHARMACOLOGICAL STUDY

The compounds of formula IA or IB in accordance with the invention cause, in vitro, blocking of the $H_3$ histaminergic receptors which control the release and the formation of cerebral histamine and, in vivo, an increase in the rate of renewal of cerebral histamine, effects which in particular establish a psychotropic action.

Antagonism of the stimulation by histamine of the central $H_3$ receptors was revealed by virtue of the method described by Arrang et al. (Nature, 1983, 302, 832–837). This method requires rat cerebral cortex sections and has made possible the pharmacological characterization of the $H_3$ receptors (Nature, 1987, 327, 117–123).

Exogenous histamine (at the concentration of 1 $\mu$M) inhibits release by approximately 50%. This effect is progressively reversed in the presence of $H_3$ antagonists, such as the compounds of the invention, added in increasing concentrations. The concentration of the latter for which the effect of exogenous histamine is reduced by half ($IC_{50}$) is determined and the apparent inhibition constant (Ki) is then calculated according to Cheng and Prusoff (Biochim. Pharmacol., 1973, 22, 3099–3108), taking into account the 50% effective concentration of histamine (EC=0.1 $\mu$M). The results are collated in the following Table II.

TABLE II

APPARENT DISSOCIATION CONSTANTS (Ki) OF VARIOUS DERIVATIVES OF THE INVENTION AS ANTAGONISTS OF HISTAMINE ON THE $H_3$ RECEPTORS OF THE BRAIN OF THE RAT. APPARENT DISSOCIATION CONSTANTS (Ki) OF VARIOUS DERIVATIVES OF THE INVENTION AS ANTAGONISTS OF HISTAMINE ON THE $H_3$ RECEPTORS OF THE BRAIN OF THE RAT.

| Example No. | Ki(nM) |
|---|---|
| 2 | 49 |
| 7 | 59 |

TABLE II-continued

APPARENT DISSOCIATION CONSTANTS (Ki) OF VARIOUS DERIVATIVES OF THE INVENTION AS ANTAGONISTS OF HISTAMINE ON THE $H_3$ RECEPTORS OF THE BRAIN OF THE RAT. APPARENT DISSOCIATION CONSTANTS (Ki) OF VARIOUS DERIVATIVES OF THE INVENTION AS ANTAGONISTS OF HISTAMINE ON THE $H_3$ RECEPTORS OF THE BRAIN OF THE RAT.

| Example No. | Ki(nM) |
|---|---|
| 15 | 35 |
| 19 | 42 |
| 22 | 11 |
| 24 | 3 |
| 36 | 20 ± 8 |
| 38 | 15 ± 4 |
| 45 | 17 ± 3 |
| 49 | 20 |
| 51 | 20 |
| 55 | 95 |
| 57 | 52 |
| 61 | 14 ± 8 |
| 67 | 15 |
| 69 | 22 |
| 73 | 24 ± 4 |
| 83 | 42 |
| 85 | 13 ± 4 |
| 86 | 18 |
| 88 | 7 ± 2 |
| 91 | 380 |
| 94 | 38 |
| 107 | 4.8 ± 0.9 |
| 110 | 35 ± 6 |
| 112 | 9 ± 5 |
| 117 | 19 ± 9 |
| 125 | 90 ± 27 |
| 130 | 12 ± 3 |
| 131 | 14 ± 6 |

The compounds of the invention cause, in vivo, after intraperitoneal or oral administration in rats, an increase in the rate of renewal of the cerebral histamine. The latter is estimated either by studying the decrease in the level of the cerebral histamine after blockage of its synthesis (Garbarg et al., Europ. Jr. Pharmacol., 164, 1–11, 1989) or by studying the increase in the level of the catabolite of histamine, telemethylhistamine (Garbarg et al., J. Neurochem., 53, 1724–1730, 1989).

This property of active $H_3$ antagonists generally makes compounds of the invention useful derivatives in human and veterinary medicine. Their therapeutic applications especially relate to the central nervous system (including as psychostimulants). The compounds of formula IA or IB are advantageously used as an active principle of medicaments which act as an antagonist of $H_3$ receptors of histamine, of medicaments possessing sedative, sleep regulating, anticonvulsant, psychostimulating, cerebral circulation modulating, antidepressant or antiulcer effects.

The present invention therefore also relates to the pharmaceutical compositions which contain, as active principle, a therapeutically effective amount of one of the compounds of formula IA or IB.

The pharmaceutical composition in accordance with the invention can be administered to man orally, perlingually, nasally, rectally and parenterally, the active principle being combined with a therapeutically suitable excipient or vehicle.

Each unit dose advantageously contains from 0.1 to 100 mg of active principle, it being possible for the doses which can be adminsitered daily to vary from 0.3 mg to 300 mg of active principle.

Another subject of the invention is the use of the derivatives in accordance with the invention for the preparation of $H_3$ antagonist medicaments according to the abovementioned forms.

The use of the compounds of formulae IA and IB in which a) X represents —NH—, the chain A the —$(CH_2)_2$— group, the chain B the —$(CH_2)_2$—O— group or the group —$(CH_2)_n$—S— and Y the phenyl or p-chlorophenyl group, b) X represents the —NHCO— group, the chain A the —$(CH_2)_2$— group and Y the methyl group (formula IB) or the chain B and Y (formula IA) represent a straight alkylene chain —$(CH_2)_n$—, n being between 1 and 4, the —$CH_2$—O— or —$CH_2$—S—$CH_2$— groups and a phenyl group, or also the —$CH_2$—$CH_2$— or —$CH_2$—S—$CH_2$— groups and the diphenyl group, or also the —$(CH_2)_3$— or —$CH_2$—S—$CH_2$— groups and the pyridyl group, or also the —$CH_2$—$CH_2$— or —$CH_2$—S— groups and the diphenyl group, or else the —$(CH_2)_3$— group and the imidazolyl or cyclohexyl group, c) X represents —NHCO—, the chain A the —$CH_2$—CH($CH_3$)— group, the chain B the —$(CH_2)_3$— group and Y the phenyl group, d) X represents —NHCSNH— or —NHCONH—, the chain A the —$(CH_2)_2$— group, the chain B the —$(CH_2)_2$— group and Y the phenyl group, whose antagonist properties of the $H_3$ receptors of histamine were disclosed during a symposium which was held at Budapest in August 1988 ("10th International Symposium on Medicinal Chemistry") and more recently at Noordwijkerhout (July 1990), is not, however, claimed.

Another subject of the invention is the use of the derivatives in accordance with the invention for preparing medicaments possessing a sedative, sleep regulating, anticonvulsant, psychotropic, psychostimulating, cerebral circulation modulating, antidepressant or antiulcer effect.

The invention further relates to a method for the treatment of pre-cited ailments according to which a medicament containing a therapeutically effective dose of a compound of general formula IA or IB, optionally in combination with a therapeutically acceptable vehicle or excipient, is administered.

We claim:

1. A method of inducing antagonist activity of $H_3$ histamine receptors in warm-blooded animals comprising administering to warm-blooded animals in need thereof an amount of a compound selected from the group consisting of a compound of the formula

IA

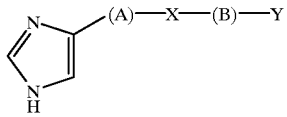

and

IB

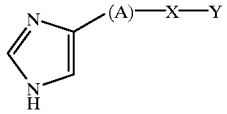

in which A is a hydrocarbon chain containing 1 to 6 carbon atoms uninterrupted or interrupted by a heteroatom selected from the group consisting of —S—, —O— and —NH—, X is selected from the group consisting of oxygen, sulfur, —NH—, —NHCO—, —N(alkyl)CO—, NHCONH—, —NH—CS—NH—, —NHCS—, —O—CO—, —CO—O—, —OCONH—, —OCON(alkyl)—, —OCONH—CO—, —CONH—, —CON(alkyl)—, —SO—, —CO—, —CHOH— and —NR—C(=NR")—NR', R and R' are hydrogen or lower alkyl and R" is selected from the group consisting of hydrogen, cyano and $COY_1$, $Y_1$ is alkoxy, B is selected from the group consisting of —$(CH_2)_n$—, n is an integer from 0 to 5, a branched alkylene of 2 to 8 carbon atoms uninterrupted or interrupted by at least one oxygen or sulfur, *and* —$(CH_2)_{n'}$—O— and —$(CH_2)_{n'}$—S— where n' is an integer of 1 or 2, Y is selected from the group consisting of alkyl of 1 to 8 carbon atoms, cycloalkyl of 3 to 6 carbon atoms, bicycloalkyl, cycloalkenyl, aryl 5- or 6-membered heterocycle selected from the group consisting of pyridyl, N-oxide-pyridyl, pyrimidinyl and pyrazinyl unsubstituted or substituted with at least one member of the group consisting of —$NO_2$, —$CF_3$, —$CH_3$, —$NH_2$, halogen, —$COOCH_3$, imidazolyl and thiazolyl and a bicyclic formed by a heterocycle as defined above to which a phenyl ring is fused, *with the proviso that*

*a) when X represents —NH—, then the substituents are not the chain A the —$(CH_2)_2$— group, the chain B the —$(CH_2)_2$—O— group or the group —$(CH_2)_n$—S— and Y the phenyl or p-chlorophenyl group,*

*b) when X represents the —NHCO— group, then the substituents are not the chain A the —$(CH_2)_2$— group and Y the methyl group (formula IB) or the chain B and Y (formula IA) represent a straight alkylene chain —$(CH_2)_n$—, n being between 1 and 4, the —$CH_2$—O— or —$CH_2$—S—$CH_2$— groups and a phenyl group, or also the —$CH_2$—$CH_2$— or —$CH_2$—S—$CH_2$— groups and the diphenyl group, or also the —$(CH_2)_3$— or —$CH_2$—S—$CH_2$— groups and the pyridyl group, or also the —$CH_2$—$CH_2$— or —$CH_2$—S— groups and the diphenyl group, or else the —$(CH_2)_3$— group and the imidazolyl or cyclohexyl group,*

*c) when X represents —NHCO—, the substituents are not the chain A the —$CH_2$—CH($CH_3$)— group, the chain B the —$(CH_2)_3$— group and Y the phenyl group,*

*d) when X represents —NHCSNH— or —NHCONH—, the substituents are not the chain A the —$(CH_2)_2$— group, the chain B the —$(CH_2)_2$— group and Y the phenyl group,* and a pharmaceutically acceptable salt, a hydrate, a hydrated salt, the polymorphic crystalline structures or the tautomeric forms thereof sufficient to induce said antagonist activity.

2. The method of claim 1 wherein the active compound has the formula

IB

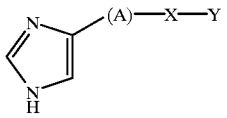

wherein A is a hydrocarbon of 2 to 6 carbon atoms, X is oxygen and Y is phenyl unsubstituted or substituted by at least one member of the group consisting of halogen, lower alkyl, —$CF_3$, —CN, —$COCH_3$, —COOR, —COR, —COOH, —$NO_2$ and

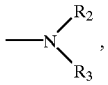

R is lower alkyl and $R_2$ and $R_3$ are hydrogen or lower alkyl and a pharmaceutically acceptable salt, a hydrate, a hydrated salt, the polymorphic crystalline structures or the tautomeric forms thereof.

3. The method of claim 2 wherein A is ethylene or propylene.

4. The method of claim 1 where the compound used is a compound selected from the group consisting of a compound of the formula

IA

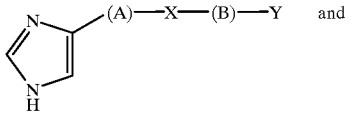

and

IB

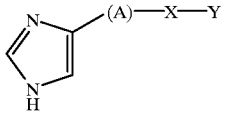

wherein A is a hydrocarbon of 1 to 6 carbon atoms optionally interrupted by a heteroatom selected from the group consisting of oxygen, sulfur and —NH—, X is selected from the group consisting of —OCO—, —COO—, —OCONH—, —OCON(alkyl)— and —OCONH—CO—, B is selected from the group consisting of —$(CH_2)_n$—, n is an integer from 0 to 5, a branched alkylene of 2 to 8 carbon atoms optionally interrupted by at least one oxygen or sulfur, —$(CH_2)_{n'}$—O— and —$(CH_2)_{n'}$—S— where n' is an integer of 1 or 2, Y is selected from the group consisting of alkyl of 1 to 8 carbon atoms, cycloalkyl of 3 to 6 carbon atoms, bicycloalkyl, cycloalkenyl, aryl, 5- or 6-membered heterocycle selected from the group consisting of pyridyl, N-oxide-pyridyl, pyrimidinyl and pyrazinyl optionally substituted with at least one member of the group consisting of —$NO_2$, —$CF_3$, —$CH_3$, —$NH_2$, halogen, —$COOCH_3$, imidazolyl and thiazolyl and a bicyclic formed by a heterocycle as defined above to which a phenyl ring is fused and a pharmaceutically acceptable salt, a hydrate, a hydrated salt, the polymorphic crystalline structures or the tautomeric forms thereof.

5. The method of claim 1 where the compound used is a compound selected from the group consisting of a compound of the formula

IA

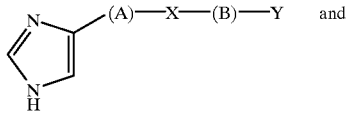

and

IB

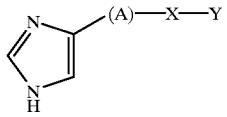

wherein A is a hydrocarbon of 1 to 6 carbon atoms optionally interrupted by a heteroatom selected from the group consisting of oxygen, sulfur and —NH—, X is selected from the group consisting of sulfur, oxygen, —N(alkyl)CO—, —NHCS—, —CON(alkyl)—, —SO— and —CHOH—, B is selected from the group consisting of —$(CH_2)_n$—, n is an integer from 0 to 5, a branched alkylene of 2 to 8 carbon atoms optionally interrupted by at least one oxygen or sulfur, —$(CH_2)_{n'}$—O— and —$(CH_2)_{n'}$—S— where n' is an integer of 1 or 2, Y is selected from the group consisting of alkyl of 1 to 8 carbon atoms, cycloalkyl of 3 to 6 carbon atoms, bicycloalkyl, cycloalkenyl, aryl 5- or 6-membered heterocycle selected from the group consisting of pyridyl, N-oxide-pyridyl, pyrimidinyl and pyrazinyl optionally substituted with at least one member of the group consisting of —$NO_2$, —$CF_3$, —$CH_3$, —$NH_2$, halogen, —$COOCH_3$, imidazolyl and thiazolyl and a bicyclic formed by a heterocycle as defined above to which a phenyl ring is fused and a pharmaceutically acceptable salt, a hydrate, a hydrated salt, the polymorphic crystalline structures or the tautomeric forms thereof.

6. The method of claim 1 wherein the compound used is a compound selected from the group consisting of a compound of the formula

IA

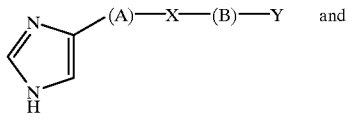

and

IB

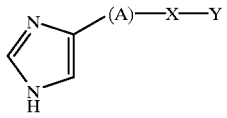

wherein A is a hydrocarbon of 1 to 6 carbon atoms optionally interrupted by a heteroatom selected from the group consisting of oxygen, sulfur and nitrogen, X is

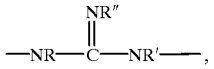

R and R' are hydrogen or lower alkyl, R" is selected from the group consisting of hydrogen, cyano and —$COY_1$, $Y_1$ is alkoxy, B is selected from the group consisting of —$(CH_2)_n$—, n is an integer from 0 to 5, a branched alkylene of 2 to 8 carbon atoms optionally interrupted by at least one oxygen or sulfur, —$(CH_2)_{n'}$—O— and —$(CH_2)_{n'}$—S— where n' is an integer of 1 or 2, Y is selected from the group consisting of cycloalkyl of 3 to 6 carbon atoms, bicycloalkyl, cycloalkenyl, pyrimidinyl and pyrazinyl optionally substituted with at least one member of the group consisting of —$NO_2$, —$CF_3$, —$CH_3$, —$NH_2$, halogen and —$COOCH_3$ and a pharmaceutically acceptable salt, a hydrate, a hydrated salt, the polymorphic crystalling structures or the tautomeric forms thereof.

7. The method of claim 1 wherein A is —$(CH_2)_n$— and n is an integer from 0 to 6.

8. The method of claim 7 wherein A is alkylene substituted with at least one methyl or ethyl.

9. The method of claim 1 wherein Y is selected from the group consisting of cyclopentyl, cyclohexyl and bicycloalkyl.

10. The method of claim 1 wherein Y is phenyl substituted with at least one member of the group consisting of halogen, lower alkyl, —$CF_3$, —CN, —$COCH_3$, —$COOR_1$, —COR, —COOH, —$NO_2$ and

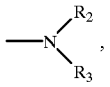

R is alkyl and $R_2$ and $R_3$ are individually hydrogen or lower alkyl.

11. The method of claim 1 wherein Y is benzothiazolyl.

12. The method of claim 1 wherein A is a saturated hydrocarbon chain interrupted by a sulfur.

13. The method of claim 1, characterized in that the compounds are chosen from:

N-((1H-Imidazol-4-yl)methyl)-5-phenylpentanamide,

N-(3-(1H-Imidazol-4-yl)propyl)-3-phenylpropanamide,

N-(3-(1H-Imidazol-4-yl)-propyl)-3-cyclohexylpropanamide,

N-(3-(1H-Imidazol-4-yl)propyl)-3-cyclopentylpropanamide,

N-(3-(1H-Imidazol-4-yl)propyl)-2-(4-chlorophenoxy) acetamide,

N-(3-(1H-Imidazol-4-yl)propyl)-2-cyclohexylacetamide,

N-(3-(1H-Imidazol-4-yl)propyl-4-cyclohexylbutanamide,

N-(3-(1H-Imidazol-4-yl)propyl)-4-methylpentanamide,

N-(3-(1H-Imidazol-4-yl)propyl)-3,3-diphenylpropanamide,

N-(3-(1H-Imidazol-4-yl)propyl)-3-(bicyclo[2.2.1]hept-2-yl)propanamide,

N-(3-(1H-Imidazol-4-yl)propyl)hexanamide,

N-(3-(1H-Imidazol-4-yl)propyl)heptanamide

N-(3-(1H-Imidazol-4-yl)propyl)octanamide,

N-(3-(1H-Imidazol-4-yl)propyl)-3-(2-cyclopenten-1-yl) propanamide, (R,S)-(±)-N-(3-(1H-Imidazol-4-yl)propyl-3-phenylbutanamide, N-(3-(1H-Imidazol-4-yl)propyl)-3-(2-pyrazinyl) propanamide, N-(4-(1H-Imidazol-4-yl)butyl)-2-cyclopentylacetamide, N-(4-(1H-Imidazol-4-yl)butyl)-3-cyclopentylpropanamide, (E)-N-(3-(1H-Imidazol-4-yl)allyl)-3-cyclopentylpropanamide, N-(3-Phenylpropyl)-3-(1H-imidazol-4-yl)propanamide, N-(2-(1H-Imidazol-4-yl)ethyl)-4-cyclohexylbutanethioamide, N-(3-(1H-Imidazol-4-yl)propyl)-3-cyclopentylpropanethioamide, N-Benzyl-N'-(3-(1H-imidazol-4-yl)propyl)urea, 3-(1H-Imidazol-4-yl)propyl ester of 3-cyclopentylpropanoic acid, 3-(1H-Imidazol-4-yl)propyl ester of benzoic acid, 3-(1H-Imidazol-4-yl)propyl ester of 4-iodobenzoic acid, 3-(1H-Imidazol-4-yl)propyl ester of 3-iodobenzoic acid, 3-(1H-Imidazol-4-yl)propyl ester of 3-iodo-4-methylbenzoic acid, 3-(1H-Imidazol-4-yl)propyl ester of 3-(4-iodophenyl) propanoic acid, 3-(1H-Imidazol-4-yl)propyl ester of 4-amino-3,5-diiodobenzoic acid, 3-(1H-Imidazol-4-yl)propyl ester of 4-(4-iodophenyl) butanoic acid, 3-(1H-Imidazol-4-yl)propyl ester of 2-(4-iodophenyl) acetic acid, 3-(1H-Imidazol-4-yl)propyl ester of 4-phenylbutanoic acid, 3-(1H-Imidazol-4-yl)propyl N-benzylcarbamate, 3-(1H-Imidazol-4-yl)propyl N-(cyclohexylmethyl) carbamate, 3-Cyclohexylpropyl 3-(1H-imidazol-4-yl)propyl ether, 3-(3,4-Difluorophenyl)propyl 3-(1H-imidazol-4-yl) propyl ether, 3-(4-Bromophenyl)propyl 3-(1H-imidazol-4-yl)propyl ether, 3-(3-Trifluoromethylphenyl)propyl 3-(1H-imidazol-4-yl) propyl ether, 1-Naphthylmethyl 3-(1H-imidazol-4-yl)propyl ether, (4-Iodophenyl)methyl 3-(1H-imidazol-4-yl)propyl ether, 4-Phenylbutyl 3-(1H-imidazol-4-yl)propyl ether, (Z)-N-(1H-Imidazol-4-yl)allyl)-3-cyclohexylpropanamide, (R,S)-(±)-N-(3-(1H-Imidazol-4-yl)butyl)-3-cyclohexylpropanamide, 3-Phenylpropyl 3-(1H-imidazol-4-yl)propyl ether, 3-Phenylpropyl 3-(1H-imidazol-4-yl)propyl sulphide, 4-[(4-Nitrobenzylthio)methyl]-1H-imidazole, 3-Phenylpropyl 3-(1H-imidazol-4yl)propyl sulphoxide, 1-(1H-Imidazol-4-yl)-7-phenylheptan-4-one, 1-(1H-Imidazol-4-yl)-7-phenylheptan-4-ol, N-Cyano-N'-[3-(1H-imidazol-4-yl)propyl]-N"-cyclohexylmethylguanidine, N-Ethoxycarbonyl-N'-[3-(1H-imidazol-4-yl)propyl]-N"-cyclohexylmethylguanidine, N-(1,1-Dimethylethoxycarbonyl)-N'-[3-(1H-imidazol-4-yl)propyl]-N"-cyclohexylmethylguanidine, N-[3-(1H-Imidazol-4-yl)propyl]-N'-cyclohexlmethylguanidine, 3-(1H-Imidazol-4-yl)propyl N-benzoylcarbamate, 3-(1H-Imidazol-4-yl)propyl N-(cyclobutylmethyl) carbamate, 3-(1H-Imidazol-4-yl)propyl N-(cyclopropylmethyl) carbamate, 3-(1H-Imidazol-4-yl)propyl (R)-(+)-N-(1-phenylethyl) carbamate, 3-(1H-Imidazol-4-yl)propyl (S)-(−)-N-(1-phenylethyl) carbamate, 3-(1H-Imidazol-4-yl)propyl N-cyclohexylcarbamate, 3-(1H-Imidazol-4-yl)propyl N-phenylcarbamate, 3-(1H-Imidazol-4-yl)propyl N-(4-methylphenyl) carbamate, 3-(1H-Imidazol-4-yl)propyl N-(4-trifluoromethylphenyl) carbamate, 3-(1H-Imidazol-4-yl)propyl N-(3-trifluoromethylphenyl) carbamate, 3-(1H-Imidazol-4-yl)propyl N-(2-trifluoromethylphenyl) carbamate, 2-(1H-Imidazol-4-yl)ethyl N-(2-phenylethyl)carbamate, 3-(1H-Imidazol-4-yl)propyl N-(4-nitrobenzyl)carbamate, 3-(1H-Imidazol-4yl)propyl N-(4-aminobenzyl) carbamate, 3-(1H-Imidazol-4-yl)propyl N-(3-nitrophenyl)carbamate, N-[2-(1H-Imidazol-4-yl)ethyl]-N-methyl-4-cyclohexylbutanamide, 3-Cyclohexylpropyl ester 3-(1H-imidazol-4-yl)propanoic acid, 3-(1H-Imidazol-4-yl)propyl N-(2-nitrophenyl)carbamate, 3-(1H-Imidazol-4-yl)propyl N-(4-fluorophenyl) carbamate, 3-(1H-Imidazol-4-yl)propyl N-(2-phenylethyl)carbamate, 3-(1H-Imidazol-4-yl)propyl N-(4-fluorobenzyl) carbamate, 3-(1H-Imidazol-4-yl)propyl N-(4-chlorophenyl) carbamate, 3-(1H-Imidazol-4-yl)propyl N-(4-chlorobenzyl) carbamate, 3-(1H-Imidazol-4-yl)propyl N-(3-iodophenyl)carbamate, 3-(1H-Imidazol-4-yl)propyl N-(2-iodophenyl)carbamate, 3-(1H-Imidazol-4-yl)propyl N-(4-iodophenyl)carbamate, 3-(1H-Imidazol-4-yl)propyl N-(3-phenylpropyl) carbamate, 3-(1H-Imidazol-4-yl)propyl N-(4-trifluoromethylbenzyl) carbamate, 3-(1H-Imidazol-4-yl)propyl N-benzyl-N-methylcarbamate, 3-(1H-Imidazol-4-yl)propyl N-benzyl-N-isopropylcarbamate, 3-(4-Chlorophenyl)propyl 3-(1H-imidazol-4-yl)propyl ether, (4-Chlorophenyl)methyl 3-(1H-imidazol-4-yl)propyl ether, Cyclohexylmethyl (1H-imidazol-4-yl)methyl ether, 3-(4-Fluorophenyl)propyl 3-(1H-imidazol-4-yl)propyl ether, p-Nitrophenyl trans-3-(1H-imidazol-4-yl)-2-propenoate, 2-{[2-(1H-Imidazol-4yl)ethyl]amino}pyrimidine, 2-{[2-(1H-Imidazol-4-yl)ethyl]amino}benzothiazole, 2-{[2-(1H-Imidazol-4-yl)ethyl]amino}pyridine, 2-{[2-(1H-Imidazol-4-yl)ethyl]amino}-3-nitropyridine, 2-{[2-(1H-Imidazol-4-yl)ethyl]amino}-5-nitropyridine, 2-{[2-(1H-Imidazol-4-yl)ethyl]amino}thiazole, 2-{[2-(1H-Imidazol-4-yl)ethyl]amino}pyrazine, 2-{[2-(1H-Imidazol-4yl)ethyl]amino}-3,6-dimethylpyrazine, 1-{[2-(1H-Imidazol-4-yl)ethyl]amino}-4-nitrobenzene, 2-{[2-(1H-Imidazol-4-yl)ethyl]amino}-5-trifluoromethylpyridine, 4-{[2-(1H-Imidazol-4-yl)ethyl]amino}-2-chloropyridine, 2-{[2-(1H-Imidazol-4-yl)ethyl]amino}-5-carbomethoxypyridine, 2-{[2-(1H-Imidazol-4-yl)ethyl]amino}-4-nitropyridine-N-oxide, 2-{[3-(1H-Imidazol-4-yl)propyl]amino}-5-nitropyridine, 2-{2-[(1H-Imidazol-4-yl)methylthio]ethylamino}-5-nitropyridine, 2-{[2-(1H-Imidazol-4-yl)ethyl]amino}-5-aminopyridine, 2-[(1H-Imidazol-4-yl)methylthio]-5-nitropyridine, 2-{2-[1H-Imidazol-4-yl]ethylthio}-5-nitropyridine, 2-{[2-(1H-Imidazol-4-yl)ethyl]thio}pyridine, 2-{[2-(1H-Imidazol-4-yl)ethyl]thio}-1H-imidazol, 4-[2-(4-Nitrophenoxy)ethyl]-1H-imidazole, 4-[2-(4-Carbomethoxyphenoxy)ethyl]-1H-imidazole, 4-[2-(4-Cyanophenoxy)ethyl]-1H-imidazole, 4-[2-(4-Acetylphenoxy)ethyl]-1H-imidazole, 4-[2-(4-Ethoxycarbonylphenoxy)ethyl]-1H-imidazole, 4-[2-(3-Nitrophenoxy)ethyl]-1H-imidazole, 4-[2-(4-Methoxyphenoxy)ethyl]-1H-imidazole, 4-[2-(4-Propylphenoxy)ethyl]-1H-imidazole, 4-[2-(4-Bromophenoxy)ethyl]-1H-imidazole, 4-[2-(3,5-Dichlorophenoxy)ethyl]-1H-imidazole, 4-[2-(2,3,4,5,6-Pentafluorophenoxy)ethyl]-1H-imidazole, 4-[2-(4-Ethylphenoxy)ethyl]-1H-imidazole, 4-[2-(3-Cyanophenoxy)ethyl]-1H-imidazole, 4-[2-(2-Cyanophenoxy)ethyl]-1H-imidazole, 4-[2-(2-Naphthyloxy)ethyl]-1H-imidazole, 4-[2-(4-Trifluoromethylphenoxy)ethyl]-1H-imidazole, and 4-[2-(1-Naphthyloxy)ethyl]-1H-imidazole, 4-[2-(4-Benzoylphenoxy)ethyl]-1H-imidazole, 4-[2-(4-Nitrophenylthio)ethyl]-1H-imidazole, 4-[3-(4-Cyanophenoxy)propyl]-1H-imidazole, 4-[3-(4-Trifluoromethylphenoxy)propyl]-1H-imidazole.

* * * * *